(12) United States Patent
    Steuer

(10) Patent No.: US 11,583,212 B2
(45) Date of Patent: Feb. 21, 2023

(54) METHOD AND APPARATUS FOR NON-INVASIVE PHOTOMETRIC BLOOD CONSTITUENT DIAGNOSIS

(71) Applicant: Robert Ricky Steuer, Ogden, UT (US)

(72) Inventor: Robert Ricky Steuer, Ogden, UT (US)

( * ) Notice: Subject to any disclaimer, the term of this patent is extended or adjusted under 35 U.S.C. 154(b) by 83 days.

(21) Appl. No.: 16/873,723

(22) Filed: Jun. 15, 2020

(65) Prior Publication Data

US 2021/0000397 A1    Jan. 7, 2021

Related U.S. Application Data

(60) Provisional application No. 62/921,397, filed on Jun. 17, 2019.

(51) Int. Cl.
    *A61B 5/1455*    (2006.01)
    *A61B 5/00*    (2006.01)
    *A61B 5/145*    (2006.01)

(52) U.S. Cl.
    CPC ...... *A61B 5/14552* (2013.01); *A61B 5/14507* (2013.01); *A61B 5/14535* (2013.01); *A61B 5/4875* (2013.01); *A61B 5/7203* (2013.01); *A61B 5/7278* (2013.01); *A61B 2562/0238* (2013.01); *A61B 2562/043* (2013.01)

(58) Field of Classification Search
    CPC .............. A61B 5/1455; A61B 5/14552; A61B 5/14535; A61B 5/7235; A61B 2562/0238
    See application file for complete search history.

(56) References Cited

U.S. PATENT DOCUMENTS

2012/0253149 A1 * 10/2012 Steuer ................ A61B 5/14546
                                                    600/322

* cited by examiner

*Primary Examiner* — Eric F Winakur

(57) ABSTRACT

A non-invasive method and apparatus utilizing a single wavelength (800 nm, isobestic) for the instantaneous, reflective, non-pulsatile spatially resolved reflectance system, apparatus and mathematics that allows for the correct determination of critical photo-optical parameters in vivo. Transcutaneous blood constituent (analyte or drug level) measurements can be determined in real-time. The "closed-form" nature of the mathematics with inclusion of other wavelengths (660 nm and 1300 nm) and a non-invasive transmissive array allows for immediate calculation and real-time display of Hematocrit, Hemoglobin, fractional tissue blood volume (Xb), Hematocrit-Independent Oxygen Saturation, fractional tissue water content (Xw) and other pertinent blood/plasma values in a variety of handheld or other like devices.

19 Claims, 12 Drawing Sheets

PCB layout

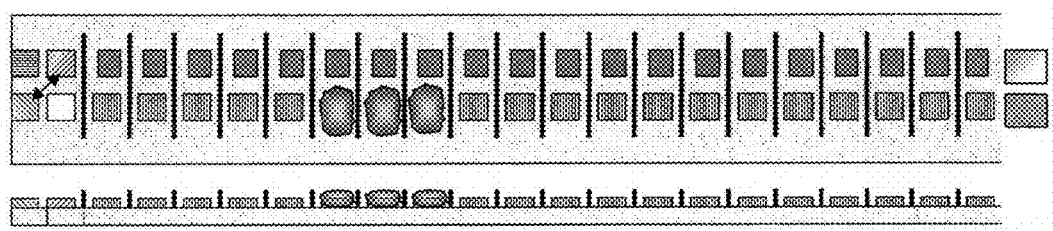

On 1 mm centers, prevent optical cross-talk between diodes & LED

- Si photodiodes
- InGaAs photodiodes
- 805 nm LED
- 660 nm LED
- 1600 nm LED
- 1300 nm LED

 Epoxy coating of proper wavelength over the photodiodes & LED

| prevent optical cross-talk, not allowing epoxy to run to next pd

FIGURE 15a (note 805nm and 660 nm LEDS added)
And switched (Note that the Silicon PDs and LEDs can be reversed, ie, an array of 805 and 660nm LEDS with 2 Silicon photodiodes at the end)

FIGURE 15b (note 805nm and 660 nm LEDS added) And switched (Note that the Silicon PDs and LEDs can be reversed, ie, an array of 805 and 660nm LEDS with 2 Silicon photodiodes at the end)

METHOD AND APPARATUS FOR NON-INVASIVE PHOTOMETRIC BLOOD CONSTITUENT DIAGNOSIS

CROSS-REFERENCE TO RELATED APPLICATIONS

The present patent application is based on, and claims priority from, U.S. provisional Application No. 62/921,397, filed Jun. 17, 2019, which is incorporated herein by reference in its entirety.

BACKGROUND OF THE INVENTION

1. Field of the Invention

The present invention relates to the photo-optical transcutaneous and continuous determination of various whole blood constituents. More specifically, the invention relates to non-invasive determination of a patient's real time Hematocrit and Hemoglobin concentration.

2. Description of Related Art Including Information Disclosed Under 37 CFR § § 1.97 and 1.98

See literature references and U.S. Pat. Nos. 5,372,136, 6,181,958, 6,671,528, 6,873,865, 5,553,616, 6,167,290, 6,339,714, 6,6,77,519 and (US 2010/0076281 A1, US 2009/0103085 A1, U.S. Pat. No. 6,606,509 B2). Certain assumptions and equations have been propagated throughout the scientific literature which has confused finding the "closed-form" solution to the governing Radiative Transport Equations. Starting in the 1940's, with additional (fiber-optic) impetus in the 1960's, and even with the Pulse Oximeter breakthrough in the 1980's, there has not been many significant advances in non-invasive photometric blood analyte measurements for the last 35 years. Even with the Pulse Oximeter's enormous success in the medical and financial realms there are several problems with its methodology which affects its inherent accuracy, such as: finger thickness, blood volume within the tissue (Xb), Arterial-Venous Oxygen Saturation difference, 940 nm versus 805 nm radiation wavelengths, background venous blood absorption, low patient blood oxygen saturation or low Hematocrit (HCT) levels, motion artifacts, low tissue perfusion (cold hands) and photometric transmissive and or reflective errors (See Schmitt, pp. 1199-1203, 1991). Additionally, other significant issues have clouded the photometric measurement modality such as: AC (pulsatile) vs. DC (non-pulsatile) techniques, transmissive vs. reflective, black skin vs. white skin and tissue analyte concentrations vs. blood analyte concentrations to name a few.

Few major advances in non-invasive analyte measurements, like Pulse Oximetry, have occurred in the past 35 years despite massive market potentials, real-time monitoring needs, and instantaneous results to the clinician, and patient dislike of needles especially for repeated monitoring.

Some of the most important constituents (analytes or drugs) to measure, in priority, are: Xb (the fractional volume of blood per total tissue volume), HCT (Hematocrit), Xw (% tissue water), HCT-independent blood oxygen saturation (O2SAT), blood Glucose (or A1C), Chemotherapeutic agents (blood level concentrations), Psychotropic drug blood level concentrations and others.

Whether exogenous (drugs) or endogenous (analytes) constituents, each constituent has its own unique electromagnetic spectrum even dissolved within the plasma milieu. It is because of this plasma milieu that the determination of Xb and HCT is so important.

By knowing the Xb, the precise quantity of blood within the total tissue space is known. Since routinely measured laboratory blood values obviously apply to the blood and not the surrounding tissue concentration of the compound in question, one can be assured that the desired constituent is measured only within the blood and, more specifically, within the plasma of the blood (again, not the tissue concentration).

By knowing the HCT, the plasma volume (1-HCT) is known and for most laboratory measured blood constituent values, it is the plasma volume that is needed to calculate the specific "blood" (or plasma) analyte concentration which can then be verified by venipuncture or finger stick. This prioritization of Xb and HCT in the mathematics will also become clearer in the mathematics below. These tissue and blood parameters are needed to determine this significant proration of the photo-optical absorption coefficient (K) and the scattering coefficient (S) discussed below.

The noninvasive determination/monitoring of these two fundamental parameters (HCT and Xb) are crucial to open up and allow vast analyte/drug titrating potential in real-time.

Why the simple HCT? Because HCT (or Hemoglobin) is so dominant in the human blood (30-50% of the blood is red cells) and since most "blood" parameters are actually within the plasma, (1-HCT) is needed to determine the correct plasma analyte values. It is also noteworthy that present day Blood Glucose Monitors (BGMs) even have HCT dependence which has not been fully eliminated.

Why Xb, this tissue perfusion value? Because perfusion in the fingertip, as an example, varies from less than 1 to 15% (15X) or typical values at a blood bank are about 2 to 6% (3X). Therefore without knowing that crucial Xb value, any measurement will be influenced more from the 3 to 15 fold Xb variations than by the constituent value one is trying to measure. To the credit of pulse oximetry, much of that 15X is cancelled out by the ratiometric techniques (but much Xb still remains and must be eliminated by frequent calibrations and a pulse is also required). Nevertheless, even within the same fingertip there exists a gradient of Xb decreasing from the knuckle to the tip itself. This gradient in Xb is further complicated with localized (regional) blood flow differences, easily seen visually in "blotchy", light to dark areas, over the fat pad. This Xb gradient must be accounted for and will be shown in the mathematics and apparatus embodiment.

It is to the solution of these and other problems that the present invention is directed.

BRIEF SUMMARY OF THE INVENTION

It is accordingly a primary object of the present invention to non-invasively determine blood constituent (analyte or drug level) concentrations in real-time.

It is another object of the present invention to provide a single wavelength, instantaneous, reflective, non-pulsatile method and apparatus and the mathematics therefore, which are the key engine to open up non-invasive blood analyte (or drug level) measurements and to titer those important blood constituent values in real-time.

These and other objects of the invention are achieved by the provision of a single wavelength, instantaneous, reflective, non-pulsatile method and apparatus for measuring the Hematocrit and Xb concentrations firstly, so that proper evaluations of the blood born constituents can be extracted from all the surrounding tissue constituents such as water, fibers, collagen, epidermis, bone, melanin, etc. The "closed-form" solution to those governing equations meeting real world boundary conditions is presented herein. The following describes the preferred embodiment of the invention: a single wavelength (800 nm, isobestic), instantaneous, reflective, non-pulsatile method, apparatus and mathematics that allows for the correct determination of critical photo-optical parameters in vivo, but non-invasively. Hence, with the present invention, non-invasive blood constituent (analyte or drug level) measurements can be determined in real-time. The "closed-form" nature of the mathematics employed by the method and apparatus not only permits better understanding of the physical interactions of the fundamental optical phenomenon, but allows for immediate calculations and display thereof in a variety of handheld or other like devices.

The method in accordance with the present invention utilizes the mathematics, algorithms, and self-normalizing directions for the spatially resolved reflectance to produce the optical coefficients necessary for physiological constituent determinations.

The apparatus in accordance with the present invention includes photon sources and detectors having specific physical arrangement and spatial characteristics, as well as requirements for how they are in contact with the patient. Yet, there is no requirement that these photon sources and detectors be collimated, coherent, monochromatic, adjustable or be aligned at specific angles as would be required by Hu (US 2009/0103085 A1).

The method eliminates the "rd" parameter, mismatched indices of refraction, by various methods: Log[R/R0] producing alphaRD/alphaCF. And alphaCF/alphaAVG (a slope average). Likewise, a complementary term is added (or multiplied) to the math to accommodate for the "rd" term, or the varying skin thicknesses. And if R0 of Log[R/R0] is selected appropriately "rd" is eliminated.

The "rastering" of A8, Ao, allow for the elimination of skin variation such as color, specular reflections, Rs, and intensity variations due to electronic heating. Rastering only is to occur for the first few samples or seconds and then that A8 value is held.

By finding the alpha, K and S independently, a "self-normalization" occurs by appropriately combining those entities so that the relationship allows for the absorbance and scattering coefficients to be combined so as to eliminate the Xb first. This leaves the HCT, and hence using that HCT to determine Xb all in real time. There are numerous ways to determine alpha (AlphaRD, alphaCF, alphaAVG-some curve fitting or by slopes of the last few data points). Similarly there are numerous ways to determine S (by curve fitting, slope of the first few radial data points—BUT before COMBINING alpha and S as explained in the equations (29 thru 32)—S must be compensated (for the "rd" issues and for the Xw (water content)).

In one aspect of the invention, only a single isobestic wavelength is required (800 nm, or 420-450 nm, or 510-590 nm, or 1300 nm, etc). The emitter used to produce those wavelengths can be a discreet single light emitting diode ("LED") or a laser diode (LD) or a spectrophotometer attached to optical fiber, etc.

No ratios of differing wavelengths are used for Hematocrit or Xb determination,

In another aspect of the invention, the method uses DC only intensities and their logarithms—no pulses or maneuvers or AC pulsatile signals are required. However, the method can also be carried out using AC (or pulsatile time dependent signals).

In still another aspect of the invention, the method and apparatus can be used for instantaneous measuring.

In still other aspects of the invention:

Mathematically a closed form solution is used, not merely fitting coefficients of an $n^{th}$ order polynomial to empirical data or a lengthy Monte Carlo simulation process.

No inflatable bladder system is required for a change in. The Xb itself is eliminated, not $\Delta$Xb (the change in Xb).

Two distinct regions (relative to the emitter) of tissue/detection are needed, 0 to 4 mm and 6 to 14 mm, for acquiring the value S and alpha independently and respectively.

Hence, this method is a "self-normalization" method, wherein with one wavelength, two physiological values are determined and alpha is normalized by S, resulting in the elimination of Xb (first) to obtain the HCT. With that HCT now known, the Xb is determined without further wavelengths, etc.

The method and apparatus can be used reflectively and/or transmissively, although reflective use is preferred.

If and only if a "point source" is NOT used, then a special "cylindrical Source Function" is required in the math (not even a Gaussian Source Function may be sufficient) and the requirements of the modified spherical Bessel functions in integration are the keys to the correct solution (see the mathematics in the Appendix hereto).

The "z" dimension is required in the math, and the "z" derivative is needed to determine the flux of photons into the detector array. This allows for the correct determination of $\mu$, which is a strong function of the indices of refraction between air and tissue and even layer thickness differences and S itself.

When solving for other parameters (other than HCT and Xb)—such as: Glucose, 02Sat, tissue water (Xw), drug levels—other wavelengths, and emitters (LEDs or LDs) may be required; but other wavelengths and emitters are not required for Hct and Xb.

The use of $r^2$ for "unmasking" the subtle changes in S in the 0 to 4 mm region, may be significant especially for use of the invention in other industries where the fundamental properties of absorption and scattering are important to determine such quantities as: "% milk fat" in a cow's milk while the cow is being milked (a way to determine cow by cow which cow is no longer producing a high enough fat content in her milk). Another example is use of the invention in the re-refining motor oil: the invention can be used for the instantaneous determination of particulate materials in the oil being reprocessed.

Other objects, features and advantages of the present invention will be apparent to those skilled in the art upon a reading of this specification including the accompanying drawings.

BRIEF DESCRIPTION OF THE SEVERAL VIEWS OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE INVENTION

Figure 1:
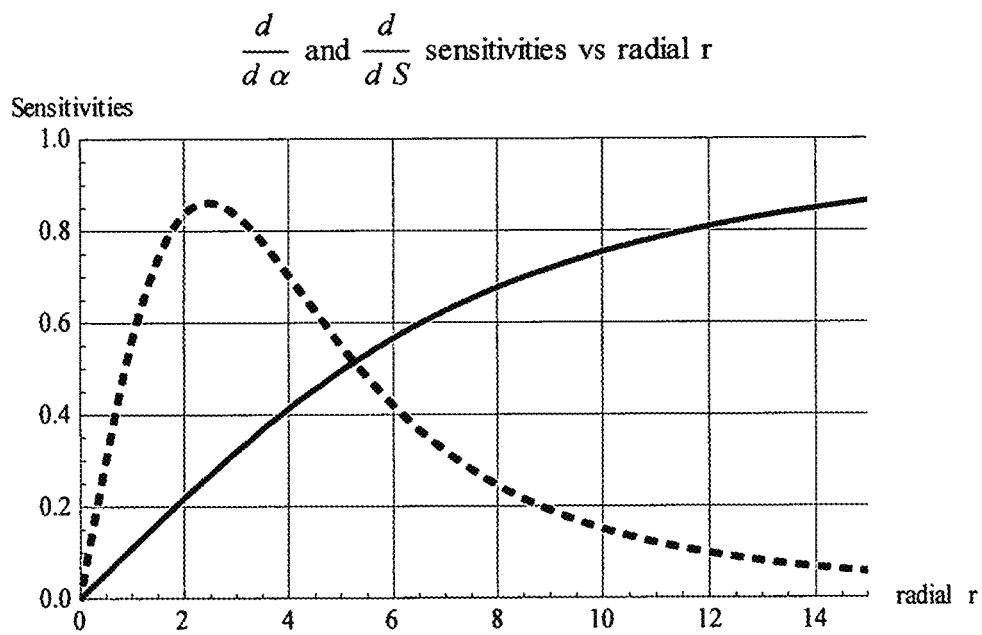
FIG. 1 is a graph illustrating the sensitivities of the radial reflectance measurements to alpha and S. Dashed line shows S sensitivity and solid line shows the alpha sensitivity. At large radial, r, the S sensitivity is negligible, hence dS/dt may even be non-existent. The method taught by Navon (US 2010/0076281 A1) would not be valid without a dS/dt in all radial tissue regions. The method by Navon would require regional tissue limitations where dS/dt may exist, be a positive value and be able to be determined, due to poor signal quality.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The present invention is described below with reference to mathematics and graphic illustrations of methods, apparatus (systems) and computer program products according to an embodiment of the invention.

As used herein, "sensor" and "detector" and "photo-detector" are used interchangeably; "emitter," "photo-emitter," "source," and "light source" are used interchangeably; and "array" is used to refer to an orderly arrangement of elements, which is not limited to a linear arrangement, but may also be matrix or circular, or a combination of linear, matrix, and/or circular arrangements. The elements in a "photo-array" as used herein include at least one emitter and at least two sensors in an array.

Reference is made to the following, the relevant portions of which are incorporated herein in their entireties, for technological background:

T. J. Farrell, et al. Tissue optical properties. *Appl. Opt.* 37, 1958, 1998.

Schmitt, J. M., Simple photon diffusion analysis of the effects of multiple scattering on pulse oximetry. IEEE Trans Biomed Eng., 38: 1194-1203, 1991 ("Schmitt 1991").

Schmitt, J. M. et al., Multiplayer model of photon diffusion in skin. J. Opt Soc. Am A 7(11): 2142-2153, 1990 ("Schmitt 1990").

Kumar, G. et al, Optimal probe geometry for near-infrared spectroscopy of biological tissue. Applied Optics 36(10): 2286-2293, 1997 ("Kumar 1997").

*Mathematical Methods for Physicists,* Ariken & Weber, 6th Ed, ELSEVIER Academic Press, 2005.

*Handbook of Differential Equations,* Daniel Zwillinger, 3rd Ed, ELSEVIER Academic Press, 1998, pp 157, 276.

Barnett, Alex. A fast numerical method for time-resolved photon diffusion in general stratified turbid media. Jr of Computational Physics 201:771-797, 2004.

Prahl, S. A., "LIGHT TRANSPORT IN TISSUE," Ph.D. thesis, University of Texas at Austin, 1988 (http://omlc.ogi.edu/~prahl/pubs/pdf/prahl88.pdf).

Theory of Light Propagation in an Absorbing and Scattering Media:

The Boltzmann Transport Equation or, in General Terms, The Modified Helmholtz Equation $\nabla^2\psi - \alpha^2\psi = Po*Fo$ Inhomogeneous 2 nd Order Differential Equation $\nabla^2\psi - \alpha^2\psi = 0$ Homogeneous 2 nd Order Differential Equation 1—Mathematical Definitions:

S is the "reduced Scattering Coefficient"

Ss is the "reduced Scattering Coefficient" of bloodless tissue

K is the Absorption Coefficient

Ks is the Absorption Coefficient of bloodless tissue

α is the "Attenuation Coefficient", (the reciprocal of the diffusion penetration depth), where:

$$\alpha^2 = 3KS$$

D is the Diffusion Coefficient, where:

$$D = \frac{1}{3S}$$

$$Po = \frac{-Io}{4\pi D}$$

Fo is a cylindrical Source Function, where:

$$Fo = e^{-\eta\rho}$$

$\rho^2$ is a point in x, y, z space, where:

$$\rho^2 = r^2 + z^2, \text{ and}$$

$$r^2 = x^2 + y^2$$

η is related to the LED/Detector apertures, or fields of view (photo-emitters and photo-detectors such as LEDs and photodiodes are constructed with pre-set apertures or fields of view, but these apertures or fields of view can be adjusted (made smaller) using masks, as well known by those of ordinary skill in the art).

μ is a dipole distance of translation in −z, where:

$$\mu = \frac{3.00}{S}$$

ψ is Fluence, the number of photons/volume in x, y, z space

The definition of other appropriate mathematical terms is found in other cited references and to some extent in the following mathematical "closed-form" solution of the inhomogeneous Modified Helmholtz Equation above. The word "inhomogeneous" has a specific mathematical meaning to those skilled in the art. Likewise, the word "homogeneous" in physiological terms has a clear meaning, as explained below.

Figure 15:
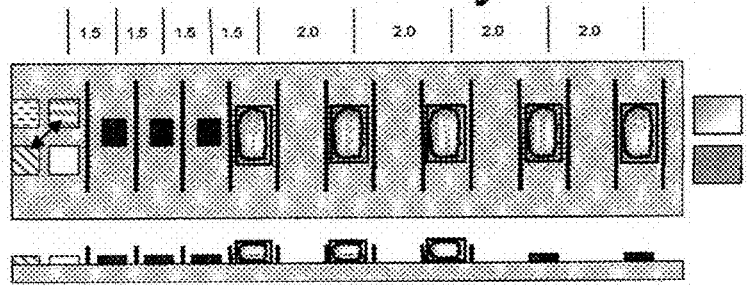
FIG. 15a illustrates a printed circuit board array including InGaAs detectors as the sensor array and $2^{nd}$ set of 805, 660 nm LEDs. Note that the photodiodes and LEDs can be reversed in the sensors.
FIG. 15b illustrates a printed circuit board array including Silicon photo detectors as the sensor array and $2^{nd}$ set of 805, 660 nm LEDs. Note that the photodiodes and LEDs can be reversed in the sensors. An example semiconductor could be the Hamamatsu S4111-16R linear photodiode array.

2—Physical Assumptions:

1. Tissue Homogeneity. Anatomically, human tissue is multi-component or heterogeneous. However, from the vantage point of the photons, the boundaries between tissue layers are ill defined. Likewise, since "the optical properties of whole tissue samples and tissue homogenates are similar . . . [and since our] source and detector apertures cover a large enough area of the skin surface . . . small inhomogeneities do not substantially affect reflectance measurements" (p 2144, Schmitt, 1990), likewise a homogeneous milieu is assumed herein for mathematical purposes. Therefore, one can consider the fingertip (foot pad, etc) as being closer in optical properties to homogeneous rather than layered tissue, with Xb being the major modifier, or prorator, of these optical parameters. However, fingertip gradients in Xb create an inhomogeneous physiological environment which must be compensated for as seen in FIGS. 15a and 15b. Nevertheless, both homogeneous and layered tissue determinations (heterogeneous) will be described in detail.

2. Unmasking. Schmitt 1990, p 2147, Farrell, 1998, p 1959, and others have shown that the Reflectance, R, is proportional to $$\frac{1}{r^2}.$$

It has been observed that this $$\frac{1}{r^2}$$

term masks the true optical coefficients and the subtleties of the nonlinear function of R versus radial r. This masking is especially onerous in the 0 to 5 mm region, where scattering is the dominant physical phenomenon. It will be seen below that when R is multiplied by $r^2$ (and then the logarithm taken), the actual S and Xb functionality with severe curvatures are clearly unmasked allowing for the determination of the true optical values. Multiplying by $r^2$ has also been used by others to "enhance the visualization of the fit", Farrell 1998. This unmasking use of $r^2$ has an additional benefit of determining S, to be described later.

3. Source Function. A Source (or Driving) Function, above described as Po*Fo, can be a simple point source, Dirac delta, a uniform light source or even a Gaussian (Finite-Impulse) Source Function. The source being considered first herein is a Cylindrical Source Function, where $$Po = \frac{-Io}{4\pi D} \text{ and}$$

$$Fo = e^{-\eta\rho}$$

in simplest form and expanded to $$Fo = e^{-\eta\sqrt{(z-\mu)^2 + r^2}}.$$

Fo is written in ρ where ρ is a point in the x, y, z space, the above Fo can be written in Cartesian coordinates for clarity now, but later it will be written in spherical coordinates when solving the mathematics. As will be appreciated by those of skill in the art, the type of light source (for example, a narrow-beam laser, fiber optic light source, or a simple LED) will affect the physical source irradiation patterns. As an example, the function:

$$Fo = e^{-\eta\sqrt{(z-\mu)^2 + r^2}}$$

if η=0, then Fo is a point source. If 0<η<1 then Fo is a cylindrical source if $r^1$, and a Gaussian source if $r^2$. The particular LED that is used in the preferred embodiment has a narrow beam width or photon irradiation pattern, and since the first photodiode detection occurs at 1.75 mm, the need for a cylindrical convolution is not utilized in the preferred embodiment (hence, η=0), but the complete method is presented so that other source profiles can be convoluted if needed. Such profiles could be:

$$e^{-\frac{S}{\mu_0}(z+3\rho)},$$

a cylindrical source, or $e^{-S_z}R(r)$, where $R(r)=U(r)-U(r-a)$, a step function, or where LED irradiation patterns can be $$\frac{1}{\rho^3}$$

or $e^{-\eta\rho}$ or $e^{-\eta\rho^2}$.

4. μ: μ can also be thought of as an "extrapolated boundary" or "the depth below the surface from which the first scattered photon emanates . . . the incident photons are converted to scattered photons within a scattering length". Schmitt, p. 1196, 1991.

5. Boundary Conditions: There is no reintroduction of photons once they have exited the finger (photons are not counted twice). But a combination of the Robins Boundary Condition and the "extrapolated" Boundary Condition will be applied. Specular reflection (Rs) will be considered later but the mismatch of the indices of refraction will be discussed in detail.

6. Xb: Xb is defined as:

$$Xb = \frac{V\text{blood}}{V\text{blood} + V\text{tissue} + V\text{water}},$$

where Vblood is the volume of blood, Vtissue is the volume of tissue and Vwater is the volume of water in the illuminated space (finger, foot, etc). An important reason for using an isobestic wavelength (i.e., 800 (780 to 815) nm or 420-450 nm, or 510-590 nm, or 1300 nm, etc) is that the need to distinguish both the arterial and venous prorations of the blood is eliminated. Otherwise, blood oxygen saturation values would be required to measure the venous and arterial blood prorations as well. However, at isobestic wavelengths the above equation becomes:

$$Xb = X\text{venous} + X\text{arterial}.$$

There is the requirement to know Xw, where other wavelengths, usually greater than 800 nm, have higher water absorption values than at 800 nm, like 1300 nm.

7. Optical Constants: Ss and Ks (bloodless tissue Scattering and Absorption coefficients) are considered constants for the human fingertip (with some variations due to Scleroderma, Reynaud's, other disease states and aging). The definitions of S, Ss, Ks, and a are discussed herein, but are well known to those skilled in the art.

8. Regions of mathematical solutions: The 0 to 5 mm region in radial r is dominated by S and in the 5 to 14+mm region in radial r, α has much greater sensitivity than S (see Bays 1996 and FIG. 1).

3—Mathematical Analysis for the Closed-Form Solution:

$$\psi = \psi_i \qquad \text{Eq. (1)}$$

is the solution to the inhomogeneous equation (Modified Helmholtz).

The Boltzmann Transport Equation simply states that: The Photon Flux, which is the rate of change of the intensity, is equal to the loss plus the gain of photons.

The Photon Diffusion Approximation Equation, PDAE, is an approximation to the Boltzmann Transport Equation, generally written as:

(PDAE): $-D\nabla^2\psi + k\psi = SF$, a source function

The PDAE retains the first (dipole) term of angular dependence (of the Boltzmann Transport Equation) and is a good approximation when K<<S, 1/S<< radial r and other geometric boundary conditions are met. This Partial Differential Equation (PDE) is seen in other physical applications and specified mathematically as the inhomogeneous Modified Helmholtz Equation. Now by dividing the PDAE by −D and including the source function, the PDAE becomes:

$$\nabla^2\psi - \alpha^2\psi = P_o * F_o, \qquad \text{Eq. (1a)}$$

inhomogeneous Modified Helmholtz Equation

Po contains the "− sign" but when Equation (1a) is solved using the Green's function (and identity) there is a "− sign" (as seen in Prahl, p 91) and as such, the "−" will be cancelled out by the following:

$$\psi = -\frac{1}{D}\left(\int_{Vol} G * PoFo\,dV + \int_{Sur,z=d} G * Q\,dS - \int_{Sur,z=0} G * Q\,dS\right) \qquad \text{Eq. (1b)}$$

The first term in Equation (1b) is what is solved, because the surface integrals will vanish since the Dirichet and Neumann boundary conditions are satisfied (Arflcen, p 597).

R, Reflection, is defined as the number of photons re-emitted or reflected out of the tissue. Mathematically this means that only the photon flux in the −z direction or the Marshak condition is of interest. As such, the solution to the PDAE can be written in terms of R and ψ and its z derivative evaluated at z=0, Equations (2) and (3) below. When considering the Robin Boundary Condition (Barnett, pp 771-779, 2003), Total Radiance is given by the proration of the fluence and the flux and Equation (2) becomes one of the best ways to extract the reflectance directly from the fluence (Barnett, pp. 771-779,2003), written as:

$$R = A1\psi(\alpha,\rho) + B1\partial_z\psi(\alpha,\rho) \qquad \text{Eq. (2)}$$

This is also Prahl's diffuse Radiance term derived over a hemispherical geometry (Prahl, pp 70-71). Generally A1 and B1 account for the detector apertures, fields of view, or refractive index mismatches. Or Equation (2) can be written as, $$R = A1\psi(\alpha,\rho) + (1-A1)D\partial_z\psi(\alpha,\rho) \qquad \text{Eq. (3)}$$

where $D*\partial_z$ eliminates D in Equation (1b)

Evaluating the flux, the z derivative, at z=0 of Equations (2) or (3), having a radial r greater than 1/S away from the source origin and determining B1 or A1 above will give the reflectance at each detector, which lay on the x axis of the fingertip. It will be shown later that for the preferred embodiment, A1 is generally small and the flux term dominates. Depending on source and detector apertures, but in the case of LEDs, A1 may be large and the fluence then modifies the measured reflectance substantially. This proration of A1 and B1 is determined empirically, generally using phantom, Intralipid mixtures, to be explained below.

Now, since the xy plane (or radial r) contains the emitter and detectors (along the x axis) and even though the flux is in the −z direction (into the xy plane) the solution will involve the z dimension (at z=0). The z parameter will be carried in the mathematics to demonstrate the dipole effect and later the source function in z, if not a point source. In other words, as r→0 the signal detected in the xy plane comes from a dipole vertically located at z=−zb below the tissue, in our case. Some literature (Kienle) cites −zb=1.96/S, the value for human data but using the photo-array of the present embodiment is −zb is 3.5/S. (−zb is often referred to as an extrapolated boundary condition or constraint). Mathematically:

$$\psi(r,z) = 0, \text{ at } z = -zb. \qquad \text{Eq. (3a)}$$

However, a more complete description of this extrapolated boundary is:

$$\mu = \frac{3.5}{S}\left(\frac{1+rd}{1-rd}\right), \quad \text{Eq. (3b)}$$

where "rd" is defined as the internal diffuse reflection coefficient. This is a strong function of the indices of refraction at the boundaries. It is this "rd" parameter or the index of refraction (which may vary dramatically), it will be shown, but which determines the correct S values. It is also another means to estimate the layer thickness (or tissue heterogeneity) when layered tissue optical parameters are to be determined.

To solve for, $\psi$, the fluence, or $\partial_z\psi$, the flux, and before evaluating $\psi=\psi_i$ it is prudent to first consider the homogeneous Modified Helmholtz Equation:

$\nabla^2\psi - \alpha^2\psi = 0$ Homogeneous 2 nd Order Differential Equation    Eq. (4)

Differential equations as above commonly have multiple solutions (or superpositions), a complementary, a particular and/or even a trivial solution, written below as:

$\psi$homo=$\psi$Homocomplementary+$\psi$Particular+ $\psi$Trivial    Eq. (5)

Numerous authors have primarily focused upon the straightforward solution to this homogeneous Equation (4), resulting in only the complementary solution:

$\psi$homo=$\psi$Homocomplementary    Eq. (6)

The reflectance can be evaluated in the xy plane with the detectors/emitter located on the x axis. Assume the fluence/flux enters the detectors perpendicular to the xy plane, then y→0 and x→r. Hence, if the solution to Equation (6) is approached using Cartesian coordinates (xyz), the results are:

$$\psi\text{Homocomplementary} = Ae^{\alpha\sqrt{(z-\mu)^2+r^2}} + Be^{-\alpha\sqrt{(z-\mu)^2+r^2}}, \quad \text{Eq. (7)}$$

where (z–μ) represents that dipole translation distance in the z space. Or stated differently, it represents a dipole strength extrapolated in –z, see Barnett, 2003, Kienle, 1996 or Allen, 1991.

But, if the reflectance is desired at any point in the xy plane and (since there is cylindrical symmetry of the source) then the solutions can be found using I and K, the Modified Cylindrical Bessel functions:

$\psi$Homocomplementary=A Io+B Ko+C I1+E K1+ . . .    Eq. (8)

If the solution is approached using spherical coordinates, the solutions are:

$\psi$Homocomplementary=A io+B ko+C i1+E k1+ . . . ,    Eq. (9)

where i and k are the Modified Spherical Bessel functions.

Notice in using the Bessel functions that there is a summation of terms and coefficients (A, B, C, E . . . ) which results in the general or complete solution. Those coefficients are determined by the boundary conditions as r→0 (d$\psi$/dr=Po) and r→∞ (or r→d, the thickness of the tissue), hence $\psi$=0, where all photons are absorbed beyond that boundary and also empirically due to detector and source fields of view. Further, notice that Equations (7), (8) or (9) are only a partial solution to the inhomogeneous PDAE—prior authors have used only these solutions and have not obtained the appropriate optical values, for α and S. If the width of the "cylindrical" source is not ignored in favor of a point source or a narrow-normal incident Dirac source—i.e., using only the Dirac as the source function in the inhomogeneous differential equation, then there is need for a Green's function approach. The Green's function is a weighting function; hence the solution will be a weighted integral over the source term.

The solutions to the above equations will, of necessity, be in three dimensions. A common method of solutions to differential equations will entail the so called "separation of variable" technique, that is:

$\psi=f(\rho, \theta, \phi)$ or $\psi=R(\rho)\Theta(\theta)\Phi(\phi)$.

Using that technique each component of the solution, (ρ, θ, φ), will give $\psi_i$.

Now consider solutions in three physical regions:
a. 5 mm to 14 mm from the light source, the PDAE is accurate and α is dominant.
b. <4 mm from the light source, the PDAE is not completely defined where S is dominant, hence, the Fokker-Planck equation, defined below, may be used to aid in the solution of the Transport Equation, below 4 mm.
c. >14 mm from the source, electronic noise (SNR), inhomogeneities (bone, blood flow gradients) and physical pressure, etc can occur.
3A—Mathematics for Determining the Solution for the Region >5 mm and <14 mm, Alpha Being More Dominant in this Region as Seen in FIG. 1.

$\psi_i=\psi_{inhomo}$    Eq. (10)

Therefore, the inhomogeneous Modified Helmholtz Equation can now be solved using a complete finite-cylindrical source function.

$\nabla^2\psi - \alpha^2\psi Po^*Fo$ Inhomogeneious 2 nd Order Differntial equation    Eq. (11)

Spherical coordinates are used because of the system geometry. It should be noted that in using the Modified Spherical Bessel functions, only io and i1, below, are integrated (and convoluted), not i2 and higher order Bessels, and integration is performed over the volume element of the sphere with $\int 4\pi r^2 dr$, where $4\pi r^2 dr$=dVol hence, the $r^2$ will cancel out the i1, k1 denominators but not the higher i2, k2 Bessels. Those higher order Bessel functions and integrals will result in imaginary values and are not suitable for the closed form discussion.

Once the partial differential equation, PDE, becomes inhomogeneous (having a driving or source function) more difficult mathematical procedures are utilized to determine the solution sets. One of the most commonly utilized techniques is the Green's function (see Arfken). Two examples are shown in Equations (12) and (13).

$\psi$inhomo=Green's Function—Eigenfunction Expansion—p 662, Arfken,    Eq. (12)

or $\psi$inhomo=Green's Function Integral-Differential Equation—pp 663-7, Arfken.    Eq. (13)

Realizing the need to deal with the z dimension, Equation (13) will be used, but solving with (13) gives a particular solution not a complementary solution, see pp 663-7, Arfken.

The complete or general solution of a PDE will be a superposition of all solutions. However, the complementary and particular solutions of the homogeneous and inhomogeneous equations noted above will not be superimposed because of the physical boundary conditions of the Green's function (Arfken, p 667).

Even though Modified Spherical Bessel functions are used in the mathematics, the finger geometry itself appears hemispherical. Equation (9) is used for reasons discussed below when solving the Integral-Differential Equation, but the hemispherical part of that solution will generate the final closed form results. To use the Green's function solutions, the homogeneous equation is utilized; hence, restating Equation (9) and using appropriate Boundary Conditions, we obtain:

$$\psi homo = A \frac{e^{\alpha\sqrt{(z-\mu)^2+r^2}}}{\sqrt{(z-\mu)^2+r^2}} + B\frac{e^{-\alpha\sqrt{(z-\mu)^2+r^2}}}{\sqrt{(z-\mu)^2+r^2}} \quad \text{Eq. (14)}$$

(the first term above could also be, io=Sinh, if desired).
However, only under the following boundary conditions:

At r=0, both A and B exist; yet as r→∞ the A term will diverge, therefore A, itself, must equal 0. Yet, this is what creates the need for and allows the use of the Green's function solution with certain boundary conditions (that is, if the actual beam width is greater than the spacing of the first few detectors):

Using Green's Function Integral-Differential Equation—Arfken & Weber, pp. 663-7 with Equation (14), we define:

$$G1 = \frac{e^{\alpha\sqrt{(z-\mu)^2+r^2}}}{\sqrt{(z-\mu)^2+r^2}} = G2 = \frac{e^{-\alpha\sqrt{(z-\mu)^2+r^2}}}{\sqrt{(z-\mu)^2+r^2}} \quad \text{Eq. (15)}$$

G1 and G2 will satisfy the homogeneous requirement of the self-adjoint operator (p 663, Arfken).

And now for the inhomogeneous solution (which includes the homogeneous operators, G1 and G2 (Arfken, pp 663-7)), Equation (13) becomes:

$$\psi inhomo1 = \psi inhomoparticular = YPzandmu, \quad \text{Eq. (16)}$$

where YPzandmu is defined as the Particular solution, Y, including "z and µ (mu)."

YPzandmu is obtained using the above Green's function solutions to the inhomogeneous 2nd Order Partial Differential Equation. YPzandmu+YPzandmu2, it will be shown, are the dominant solutions of ψ.

Using Green's Function Integral-Differential Equation—pp 663-7 Arfken, with Equation (15) satisfying the homogeneous requirement of the self-adjoint operator, Arfken p 663, we determine YPzandmu as (see the Appendix for detailed mathematics):

Equation (17) is only the first term (io, ko) of the complete expansion, but includes the convolution of the cylindrical source function, $Fo = e^{-\eta\rho}$.

$$YPzandmu = \quad \text{Eq. (17)}$$

$$\left(\frac{e^{-\alpha\sqrt{(z-\mu)^2+r^2}}}{\sqrt{(z-\mu)^2+r^2}}\int_0^{\sqrt{r^2+(z-\mu)^2}}\left(\frac{e^{\alpha t}}{t}\right)\right.$$

$$(e^{-\eta t})\int_0^\infty \cos[\alpha(z1-z2)]d\alpha(t^2)dt + \frac{e^{\alpha\sqrt{(z-\mu)^2+r^2}}}{\sqrt{(z-\mu)^2+r^2}}$$

-continued $$\int_{\sqrt{r^2+(z-\mu)^2}}^\infty \left(\frac{e^{-(\alpha t)}}{t}\right)(e^{-\eta t})\int_0^\infty \cos[\alpha(z1-z2)]d\alpha(t^2)dt\right)$$

where $\rho = \sqrt{(z-\mu)^2+r^2}$, where t is not time, but rather a point defined as 0<t<ρ, or ρ<t<∞. Note the convolution is integrated or "convoluted" over "multiple points", not a specific point or source diameter.

$\int_0^\infty \cos[\alpha(z1-z2)]d\alpha$ gives the z component where pages 599, 601, 609, 792, 944 and 987 (Arfken) give the Fourier Integral Transforms with the Ko Bessel resulting in:

$$yp1dtimcylinderwithz = \quad \text{Eq. (17a)}$$

$$\frac{-1}{\left(\sqrt{(z-\mu)^2+r^2}\right)^1}\left(e^{-\alpha\sqrt{(z-\mu)^2+r^2}}\int_0^{\sqrt{r^2+(z-\mu)^2}}\left(\frac{e^{\alpha t}}{t}\right)(e^{-\eta t})(t^2)dt + \right.$$

$$\left. e^{\alpha\sqrt{(z-\mu)^2+r^2}}\int_{\sqrt{r^2+(z-\mu)^2}}^\infty \left(\frac{e^{-(\alpha t)}}{t}\right)(e^{-\eta t})(t^2)dt\right)$$

Equation 17a is the "convolution" of a Green's function solution with a Cylindrical Source Function (a function of η and r) under the boundary conditions of the Green's function.

Now YPzandmu2, the second term of the modified spherical Bessel solution: Equation (18) is the second term (i1, k1) of the complete integral expansion.

$$Ypzandmu2 = \quad \text{Eq. (18)}$$

$$\frac{-1}{\alpha\left(\sqrt{r^2+(z-\mu)^2}\right)^2}\left(e^{-\alpha\sqrt{r^2+(z-\mu)^2}}\left(\alpha\sqrt{r^2+(z-\mu)^2}+1\right)\right.$$

$$\int_0^{\sqrt{r^2+(z-\mu)^2}}(\alpha t \cosh[\alpha t] - \sinh[\alpha t])$$

$$(e^{-\eta t})dt\int_0^\infty \cos[\alpha(z1-z2)]d\alpha +$$

$$\left(\alpha\sqrt{r^2+(z-\mu)^2}\cosh\left[\alpha\sqrt{r^2+(z-\mu)^2}\right] - \sinh\left[\alpha\sqrt{r^2+(z-\mu)^2}\right]\right)$$

$$\int_{\sqrt{r^2+(z-\mu)^2}}^\infty((\alpha t+1)e^{-(\alpha t)})(e^{-\eta t})dt\int_0^\infty \cos[\alpha(z1-z2)]d\alpha\right)$$

where $\rho = \sqrt{(z-\mu)^2+r^2}$ $\int_0^\infty \cos[\alpha(z1-z2)]d\alpha$ gives the z component where Arfken pp 599, 601, 609, 792, 944 and 987 give the Fourier Integral Transforms with the K1 Bessel resulting in:

$$ypcylasphi1k1 \quad \text{Eq. (18a)}$$

$$withz = -\frac{r}{\alpha\left(\sqrt{r^2+(z-\mu)^2}\right)^3}\left(e^{-\alpha\sqrt{r^2+(z-\mu)^2}}\left(\alpha\sqrt{r^2+(z-\mu)^2}+1\right)\right.$$

$$\int_0^{\sqrt{r^2+(z-\mu)^2}}(\alpha t \cosh[\alpha t] - \sinh[\alpha t])(e^{-\eta t})dt +$$

-continued $$\left(\alpha\sqrt{r^2+(z-\mu)^2}\cosh\left[\alpha\sqrt{r^2+(z-\mu)^2}\right]-\sinh\left[\alpha\sqrt{r^2+(z-\mu)^2}\right]\right)$$

$$\int_{\sqrt{r^2+(z-\mu)^2}}^{\infty}((\alpha t+1)e^{-(\alpha t)})(e^{-\eta t})dt\right)$$

Only the io, ko, i1 and k1 Bessel functions are convoluted because if the Cylindrical Driving Function is multiplied within the integral by higher order Bessels, then a non-numeric or non-imaginary integration is not possible. But allowing Fo to be a Cylindrical Driving Function, which is more like the real world for certain fiber optical, LED or LD arrangements, the other functions, G1 and G2, in the integrand, when multiplied by Fo, have to be integrable in order to obtain a "closed-form" solution, as seen above in Equations (17-18).

So the solution to Equation (10) is a superposition of Equations (17a) and (18a), or even one or the other by itself, defined by the physical parameters of the preferred embodiment, as:

$(\psi_i=\psi_{inhomo})$=z$\eta$hemicylsph+z$\eta$hemicylsphi1k1,   Eq. (19)

where:

$$z\eta hemicylsph = \frac{-2}{\rho}\partial_\rho z\eta cylinder \text{ and}$$

$$z\eta hemisphi1k1 = \frac{-2}{\rho}\partial_\rho z\eta cylsphi1k1$$

are the hemispherical portion of the complete solution, where
z$\eta$cylinder=$\partial_z\psi_0$ and
z$\eta$cylsphi1k1=$\partial_z\psi_1$,
both evaluated at z=0.
and where:
$\psi_0$=yp1dimcylinderwithz and
$\psi_1$=ypcylsphi1k1withz.

In the present mathematical discussion and physical embodiment thereof in the apparatus according to the invention, only the flux term, not the fluence, dominates the detectors (A1=0, Equation (3) above). As mentioned however, by changing the field of view of the LED or detectors, the fluence term will contribute with 0<A1<1. That field of view can be altered by using "flat" surface mount LEDs or cylindrical optical fibers. Therefore to determine the degree of proration of the A1 and B1 terms in Equation (2) the following ratio is important:

$$\text{Log}[R/R0] = \frac{\psi}{\psi 0} \qquad \text{Eq. (19a)}$$

where R0 is a measured reference reflection, in the present embodiment, measured at 1.75 mm and $\psi_0$ is the fluence at 1.75 mm. R are the measured values at the radial r of the array. $\psi$ is the fluence, described in Equation (15) as G2 or $\psi$ in Equation (19a) can also be described, if A1 is very small, by the flux as $$\frac{dG2}{dz}.$$

The linearity or curvature of Equation (19a) versus r determines the magnitude of the proration factor A1. The slope of Log[R/R0] is defined as alphaRD (determined by curve fitting or simple radial derivative measurements). Likewise, this Log[R/R0] ratio with R0 chosen at about 4 to 7 mm will be virtually independent of S (at a constant value, but with minimal dS/dt, which may even be neglected) and be a function of K.

YPzandmu+YPzandmu2 are the dominant terms (>4 mm and <14 mm) of Equation (1a). See FIGS. 2 and 3, which are graphs of data of two patients (the small and large dots) with Equation (19) through those data points showing the fit of Equation (19) to the data.

DRR is the well-known time derivative of the logarithm of the reflectance, because of the change in Xb of the tissue as a result of pulsatile blood flow. More specifically and mathematically correct, using the chain rule, Equation (20) is obtained:

$$DRR = \frac{\frac{\partial R}{\partial t}}{R} = \frac{1}{R}\left(\frac{\partial R}{\partial \alpha}\frac{\partial \alpha}{\partial Xb}\frac{\partial Xb}{\partial t}\right), \text{ or} \qquad \text{Eq. (20)}$$

$$\frac{\partial \text{Log}(R(\alpha,S)r^2)}{\partial Xb} = \frac{\partial \text{Log}(R)}{\partial \alpha}\frac{\partial \alpha}{\partial Xb} + \frac{\partial \text{Log}(R)}{\partial S}\frac{\partial S}{\partial Xb} \qquad \text{Eq. (20a)}$$

but this quantity typically is multiplied by ←Xb/∂t. See FIG. 3 with actual patient data.

3B—Mathematics for Determining the Solution for the region <5 mm Where S has Much Greater Optical Sensitivity than α, Must Also be Included.

Referring to FIG. 1, the dashed line gives the d (Log[R])/dS, or sensitivity to S.

$\psi=\psi_i$   Eq. (21)

will now include the 0 to 5 mm effects of S, α and K.

This region <5 mm is important for many reasons, but simply stated it is the region that determines the profile or pattern of the incident light within the tissue. Mathematically, numerous approaches are employed to model how photons injected into tissue, even with laser-like narrow beams, will "spread" and ultimately "blur" or "smear" an image (especially seen in optical tomography).

Hence, authors have used the Monte Carlo simulation approach to define more accurately the 0 to 5 mm region. But, this numerical crunching is like polynomials being fit to the data and then empirically finding the coefficients. Many authors have recognized the need to develop a compact simple mathematical form of the lengthy and time consuming Monte Carlo simulations. Some developed a polynomial which described a Point Spread Function, PSF, allowing faster parameter determinations which helped describe this blurring function.

Others have used the Fokker-Planck equation (a Probability Density PDE, Zwillinger, p 276) to describe this 0 to 5 mm region. But, this equation is merely a special case of the Parabolic Partial Differential Equations I, PPDEI (see Zwillinger, p 157; and also, see Farlow, pp 58-60). These types of PDEs basically describe the same phenomenon: diffusion plus drift or diffusion plus convection or diffusion plus an image charge (dipole) or diffusion plus lateral heat loss.

Using PPDEI, note the Laplacian Operator, $-D\nabla^2\psi$ which deals with the "heat" or diffusion-only component (see Arfken, p 614, Farlow, p 58-60, and others). Recognizing that S is dominant and that the "drift" or "convection" or "lateral heat loss" (K) terms also contribute to the spreading or blurring, the Fokker-Plank or PPDEI becomes:

$$\frac{d\psi_S}{dt} = D\frac{d^2\psi_S}{dr^2} - D2\frac{d\psi_S}{dr} - D3\psi_S \qquad \text{Eq. (22)}$$

While the above is technically sound, Barnett's discussion of the dipole (as in heat transfer, Barnett p 11, 2003) incorporates K, absorbance, very simply. Allen's discussion of the dipole effects are similarly straight-forward (pp 1621-1628, 1991). These solutions can also be given as a so-called "Ansatz product", Arfken, p 611 or Farlow's, pp 58-60, or Zwillinger's form (p 157) and becomes:

$$\psi = e^{-bK}(z\eta cylsphi1k1) = e^{-3\frac{a^2}{3S}}(z\eta cyclsphi1k1), \qquad \text{Eq. (23)}$$

We see here the diffusion term, ($z\eta cylsphi1k1$), and the lateral loss, $e^{-bK}$, components.

The term D3 in Equation (22) can be determined empirically as ~b K, where now D3=K, and b=−3. However, using Allen's approach that same lateral loss component can be written as, $$e^{-b\frac{a1}{S}},$$

where empirically b~3. "b" will change with photo-optic parameters such as fiber optic (or LED) field of view, beam widths, detector apertures, etc. In other words, D3, the "lateral heat flow rate" is the absorption of photons, a "lateral photon flow rate" or specifically a photon loss in the x, y dimensions. As mentioned, b K, captures this flux in x and y. The detectors/emitter array is along x. This is under the assumption that A=0 or the system being flux dominated.

Incorporating the above functions in S, K, α, the $$\frac{1}{r^2}$$

term and then taking the Logarithm, Equation (23) becomes, the final solution with NO convolution shown (a point source function is described in Equation (24), but see the Appendix for solutions with source convolutions):

$$\log r2Rx = \text{Log}(R*r^2): \qquad \text{Eq. (24)}$$

$$\log r2Rx = A8 + 2\text{Log}[r] +$$

$$\text{Log}\left[((1-Rs)\mu e^{-3K})\frac{e^{-a\sqrt{r^2+(-\mu)^2}}}{\left(\sqrt{r^2+(-\mu)^2}\right)^2}\left(B\left(\alpha+\frac{1}{\sqrt{r^2+(-\mu)^2}}\right)+\right.\right.$$

$$\left.\left.E\left(\alpha^2+\frac{2\alpha}{\sqrt{r^2+(-\mu)^2}}+\frac{2}{\left(\sqrt{r^2+(-\mu)^2}\right)^2}\right)\right)\right],$$

where A8=17.52 (incident intensity) with B=1 and E=0 as proration factors of the ko and k1 Bessel functions in Equation (9) and dependent on light source optics for this present embodiment. Yet depending on those optics, the E value will also contribute and that E value can be determined empirically and with the boundary conditions, hence allowing the k1 Bessel to be significant (see Equation (19)). Mathematically, however, nothing limits the above from higher order Bessel functions. A8 in the present Equation (24) is shown as a constant value (17.52). However, as seen in Equations (2) and (3) the A1 (or fluence) term can also be included in the parameter, A8. This fluence term has the form of Equation (15), specified as G2.

Figure 2:
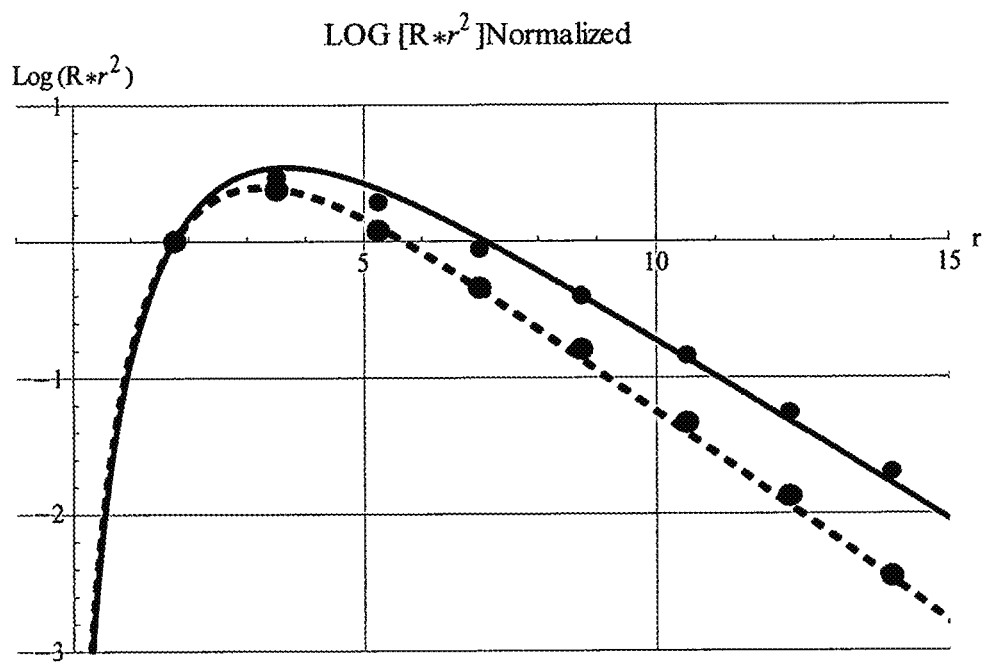
FIG. 2 is a graph of data of two patients (small and large dots) compared with Equation (19) through those data points (dashed and solid lines).
Figure 3:
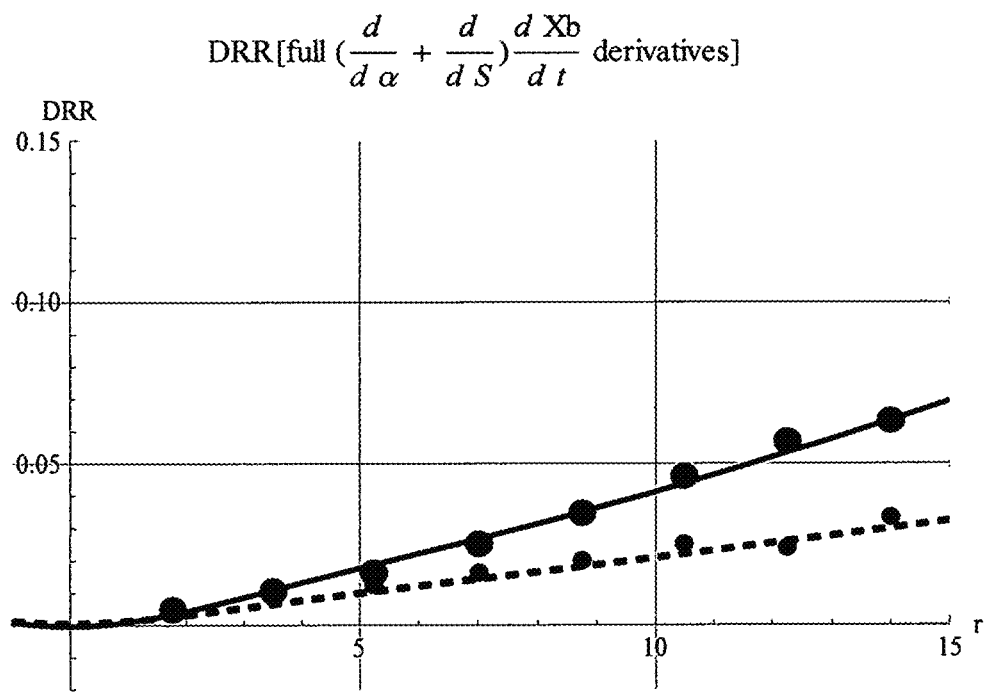
FIG. 3 is a graph of the data for the same two patients as in FIG. 2, but showing the agreement of the mathematics in Equations (20 and 20a) to the actual human data.
Figure 4:
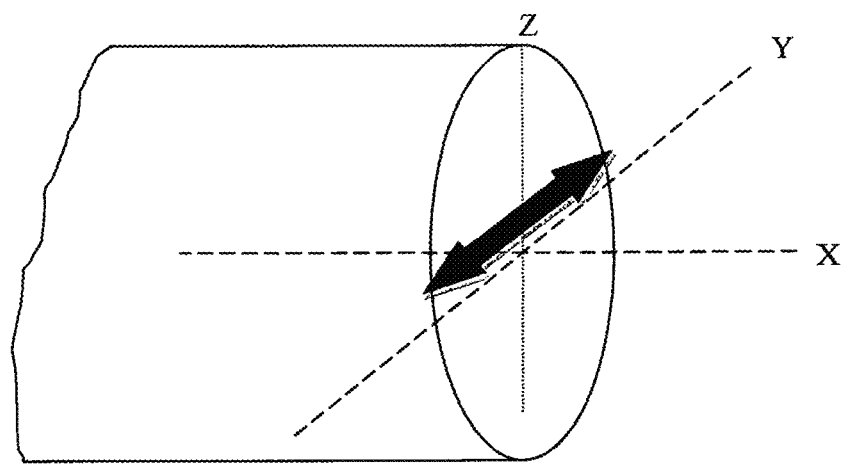
FIG. 4 illustrates a cylindrical form representing the human finger geometry.

Note again that YPzandmu and/or YPzandmu2 are the dominant contribution to the complete solution (see FIGS. 2 & 3). These graphs will elucidate that this 0 to 4 mm region is crucial in determining S.

The complete solution Equation (24) is graphed in the validation section, see FIGS. 5-11.

4—Validation of the Mathematics, Methods and Preferred Embodiment of the Apparatus.

Real data: Equation (24) can be verified for fit and accuracy using various types of actual data: a well-known phantom material of 1% Intralipid and varying amounts of human blood, or non-pulsatile "DC" human fingertip data and even pulsatile "AC" fingertip data. The Equation (24) fits the human and phantom data with minor adjustments to the phantom optical parameters, Ks, Ss, Xs and Xw, which are in keeping with other authors' Ks, Ss, Xs and Xw values. Those coefficients are described herein.

A—Phantom or Intralipid experiments. Phantom mixtures of Intralipid and whole blood was prepared and used to fill phantom fingers made from the fingers of 1" diameter latex gloves. The mixtures had varying Intralipid concentrations.

Figure 5:
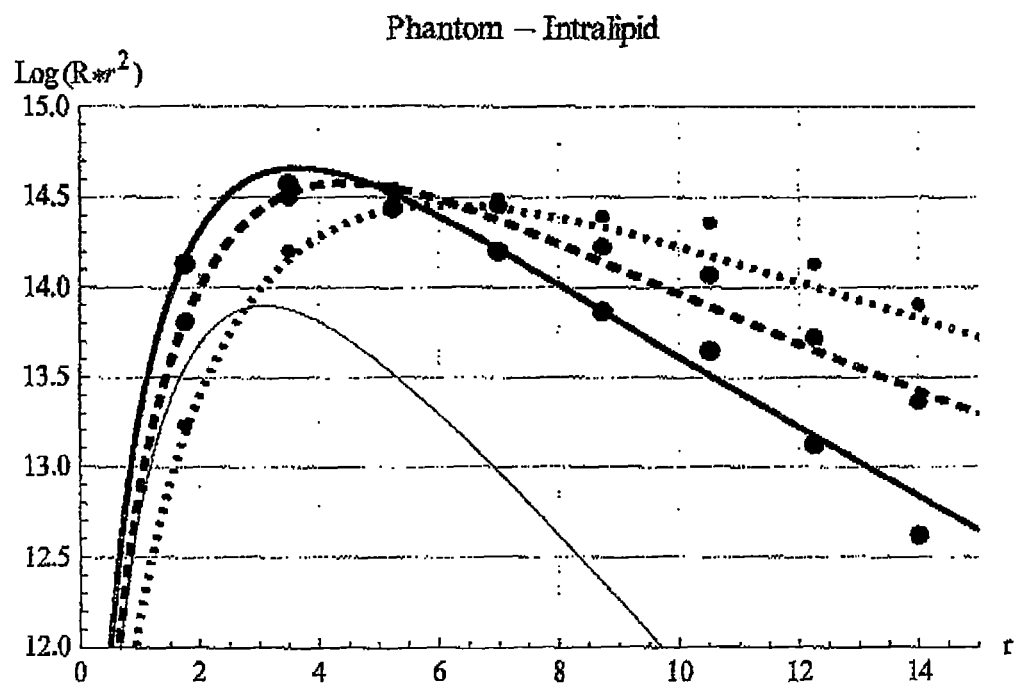
FIG. 5 is a graph illustrating the DC measurement of varying Intralipid concentrations. The dotted line=0.5% Intralipid, the dashed line=1.0% Intralipid, and the solid line=2.0% Intralipid. The thin solid line is 1% Intralipid with 10% of whole human blood (HCT=0.50).

FIG. 5 shows the DC measurement of the varying Intralipid concentrations (the background) using one wavelength at 805 nm.

There is good fit of Equation (24) to the data points. The $r^2$ unmasking accentuates the S effect (0 to 5 mm) of those Intralipid concentrations and the thin solid line shows the K effect.

B—Another Intralipid experiment shows varying the Xb, from 1.25% Xb to 9.5% Xb, with a constant HCT=.50 in the 1% Intralipid mixture. Results shown in FIG. 6 indicate an excellent fit of the mathematics and the data points.

C—Yet another experiment confirming the accuracy of Equation (24) is to match the exact relationship between alpha and Xb (see below for that function). Recall that each of the Xb values is known because of the simple mixing of the appropriate aliquots of blood with Intralipid. See FIG. 6a. This good data and mathematics fit indicates that Equation (24) and the curve fitting algorithm (to be discussed below) return the appropriate alpha and Xb relationship.

Relationship of Alpha and S

From the literature, α, K and S are related by:

$$\alpha = \sqrt{3*K*S}$$

Figure 7:
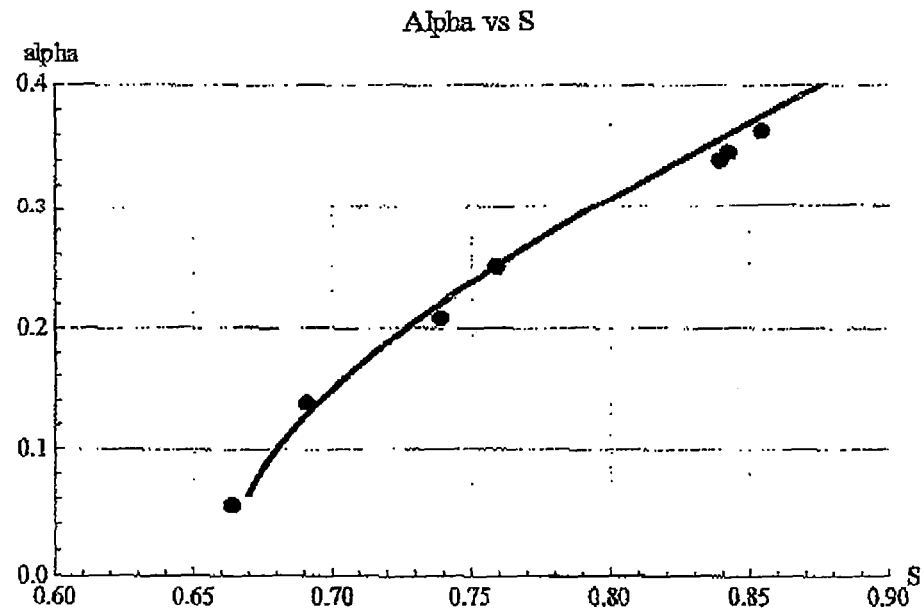
FIG. 7 is a graph of alpha versus S, where the actual data points of this Intralipid and Xb mixture, represented by black dots, match very closely Equation (24), represented by the solid line.
Figure 8:
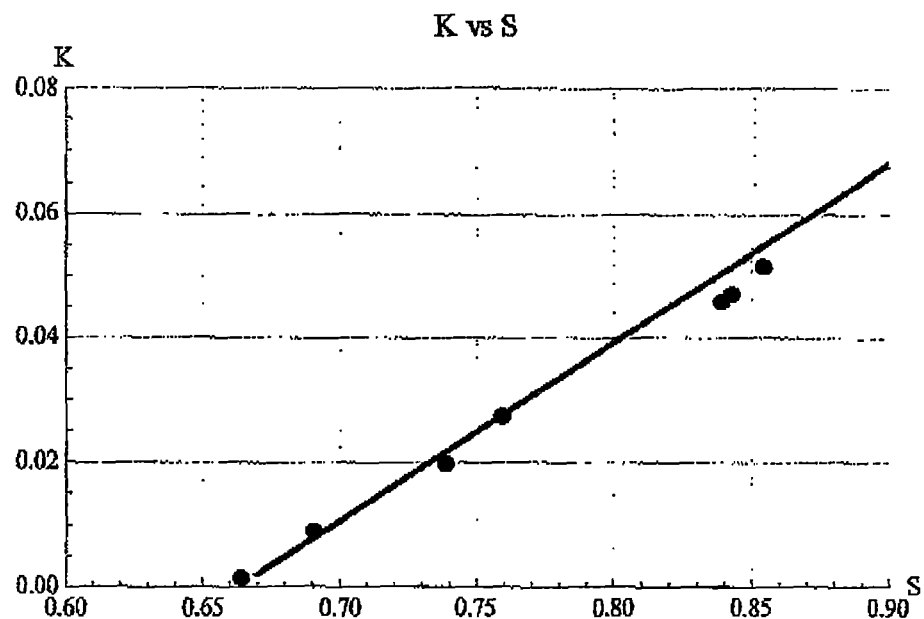
FIG. 8 is a graph of K versus S, where the data points and Equation (24) show the linearity as predicted.
Figure 9:
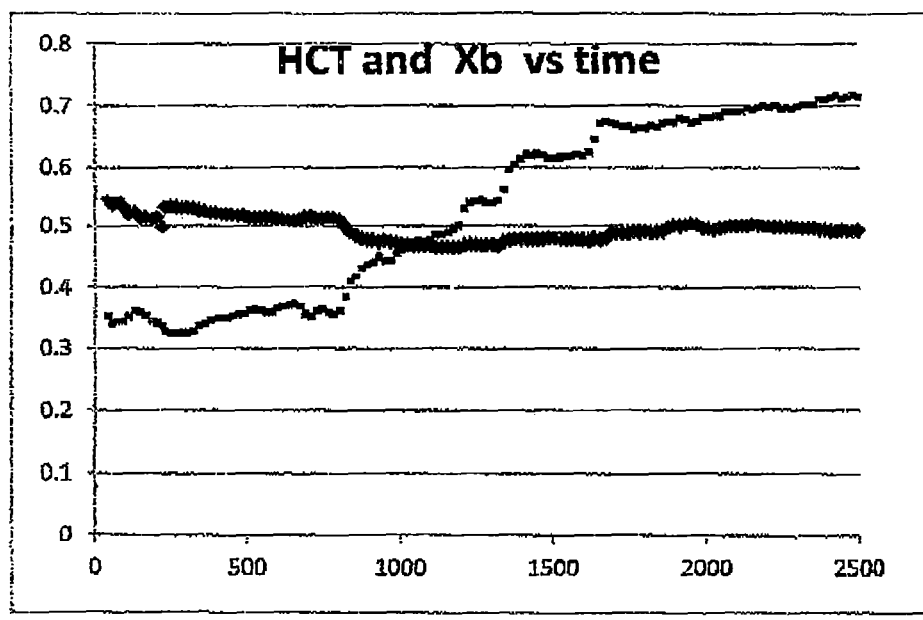
FIG. 9 is a graph of HCT and Xb versus time. HCT (large diamonds), was monitored over time, being constant while large Xb changes occurred throughout this experiment. These changes were produced by raising and lowering the hand to extremes (Xb, small squares). In order to see the Xb change in the same graphic as the HCT, the Xb values were multiplied by 10.
Figure 10:
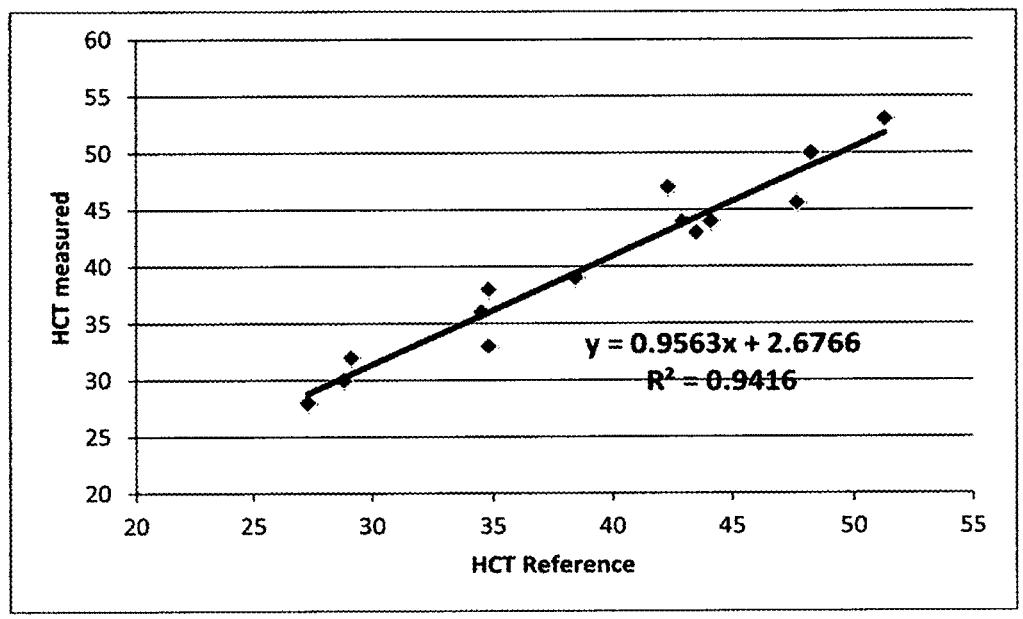
FIG. 10 is a graph of data for a 15 patient run with the apparatus and method according to the invention, in which HCT is measured versus HCT reference (Coulter Counter).
Figure 11:
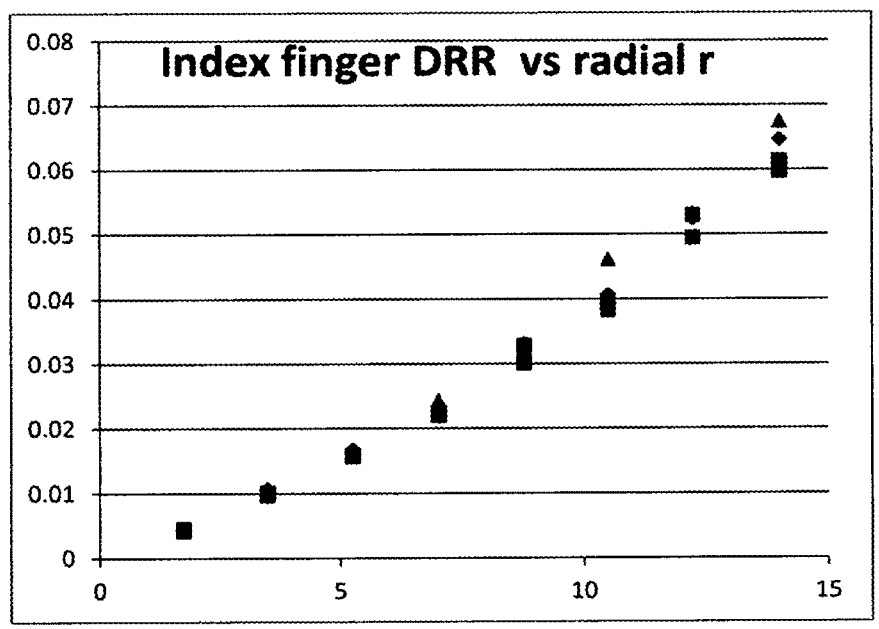
FIG. 11 is a graph showing a "small signal" change in Xb over time, typically caused by the human pulse, but showing the correlation with Equation (24).

FIG. 7 shows alpha versus S. The mathematics predicts and shows that precise square root functional relationship between alpha and S.

Relationship of K and S

The mathematics in Equation (24) and graphics again shows that K and S behave as the mathematics above predicts—now a linear function between K and S.

The parametric plotting of K versus S cancels out Xb and leaves a function of HCT (see Equation set (28a)-(28j) here below). This is significant because numerous optical parameters and human physiology can change the Xb (perfusion), like calluses, raising and lowering the hand, warm and cold hands, coughing, Valsalva, etc.

HCT is Determined Directly from K vs. S

Human experiments. Using only the DC (non-pulsatile), one wavelength, 805 nm method, the resulting HCT graphic of FIG. 9 indicates that the Xb has been cancelled out and the true HCT function is obtained. The Xb change that occurred in this experiment was produced by simply raising and lowering the hand.

Note that HCT versus time is quite "flat" or almost independent of Xb at HCT=0.50.

But Xb versus time shows a 200% change. Therefore from Equation (24) K and S can be determined and by self-normalization (using a single isobestic wavelength) the cancellation of these very large Xb changes is accomplished.

It should be noted that in photometry mathematics, the HCT is always multiplied by Xb or HCT*Xb (described in Equations (28a)-(28j) below). Therefore what FIG. 9 also shows and infers is that at a constant Xb this apparatus and method can also accurately measure a 200% change in HCT. Since this graph has 155 unique data points this is as if 155 patients, who had different HCTs, were just run.

To verify that above statement further, fifteen patients were tested demonstrating the Xb cancellation and resulted in HCT determinations of very good accuracy and correlation.

It is also clear that AC or "pulsatile" one wavelength 805 nm data and information can also give important verification to Equation (24). To obtain the DRR, multiple data sets of the $\alpha$ and S derivatives of Equation (24) was co-temporaneously done, using the Equations (20) and (20a), with the correlating results shown in FIG. 11.

The reason the DRR is also important for verification is because many possible mathematical functions could fit Equation (24) the Log R versus radial r data quite well. But, when the $\alpha$ and S derivatives are taken, those other functions break down showing severe inaccuracies compared to human data using this AC (pulsatile) method. Hence, because of those inaccuracies, including all the Xb derivatives of Equation (24) will be shown, beginning with Equation (20a) again. Kb and Sb will be described below in Equations (28a)-28(j) below.

$$\frac{\partial \text{Log}(R(\alpha, S)r^2)}{\partial Xb} = \frac{\partial \text{Log}(R)}{\partial \alpha} \frac{\partial \alpha}{\partial Xb} + \frac{\partial \text{Log}(R)}{\partial S} \frac{\partial S}{\partial Xb} \quad \text{Eq. (20a)}$$

$$\frac{\partial \alpha}{\partial Xb} = \frac{3}{2\alpha}\left(K\frac{\partial S}{\partial Xb} + S\frac{\partial K}{\partial Xb}\right) \quad \text{Eq. (25)}$$

$$\frac{\partial S}{\partial Xb} = (Sb - Ss) \text{ as a function of } Hct \quad \text{Eq. (26)}$$

must be multiplied by $\partial Xb/\partial t$.

$$\frac{\partial K}{\partial Xb} = (Kb - Ks) \text{ as a function of } Hct \quad \text{Eq. (27)}$$

must be multiplied by $\partial Xb/\partial t$ since a human pulse occurs over a time period. It should be noted that "pathlengthening terms, PL" (dlog(R)/dalp and dlog(R)/dS) are included in Equation (20a). These PL terms are non-trivial functions of $\alpha$, S and radial r (reflection) or "d" (transmission).

In Equation (25) we note that many authors neglect the $$\frac{\partial S}{\partial Xb}$$

term because it is multiplied by K, which is usually very small, ie the assumption is that K<<S. However, the full derivatives in $\alpha$ and S are needed to provide the correct offset in DRR at r=0, when time derivatives are used.

Figure 6:
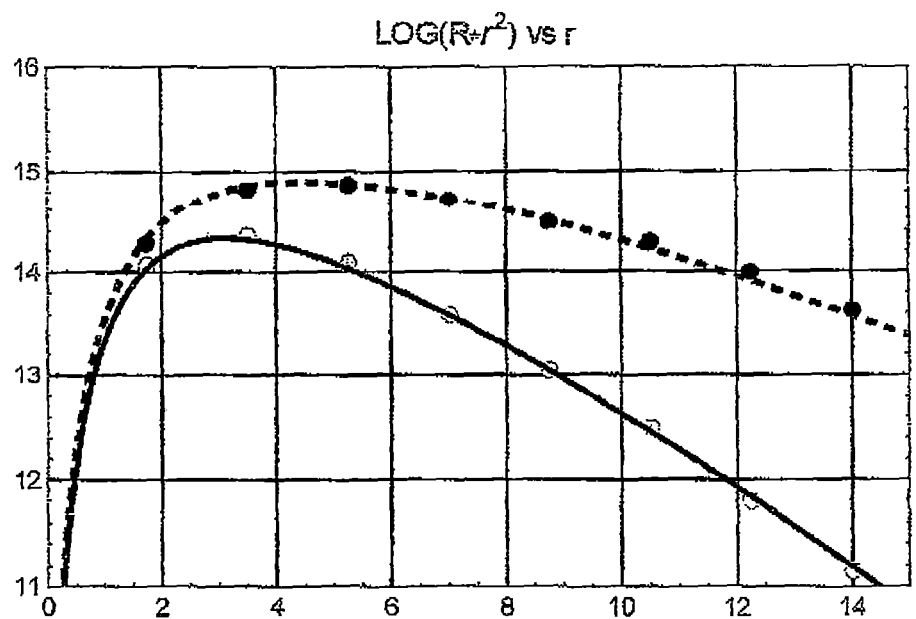
FIG. 6 is a graph illustrating data sets for two different Xb concentrations. The dashed (Xb=1.25%) and solid (Xb=9.5%) lines are the Equation (24) fit to the respective data points.
Figure 6A:
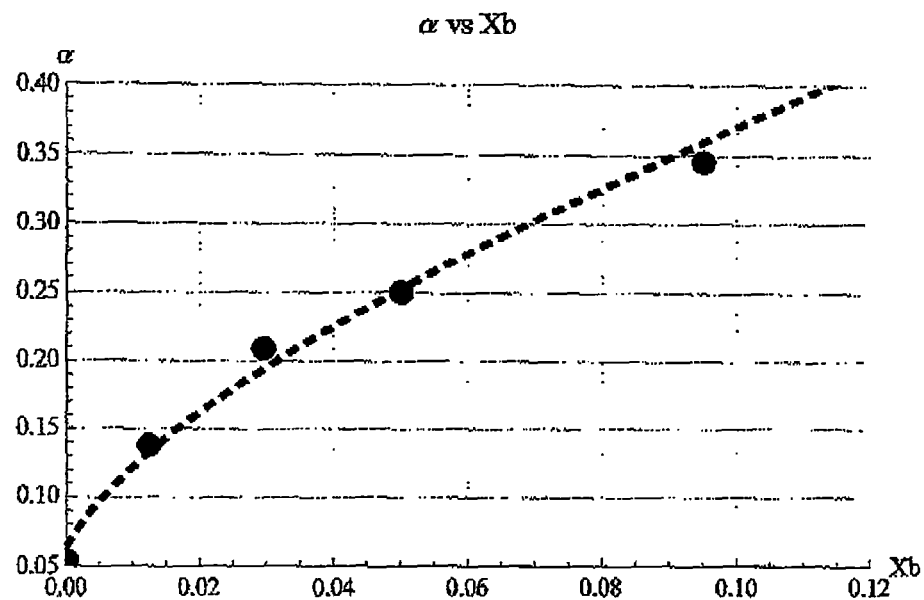
FIG. 6a is a graph in which Alpha (determined using Equation (24)) is shown as function of Xb. The dashed line is Equation (24) through the data points of known Xb concentrations.

Likewise, FIGS. 2, 5 and 6 show the effect of unmasking the subtleties in curvature not easily seen while merely plotting the Logarithm [R] versus radial r. Even though $r^2$ unmasking is just a mathematical maneuver, it does allow better understanding of the various regions for spatial resolution of reflected light.

D—Other Mathematical Definitions, Equations and Coefficients

To Solve for $\alpha$, S, Using Only one Isobestic Wavelength, DC Measurements and Equation (24)

A—Known optical coefficient values from the literature:

Some known absorption, K, and reduced scattering, S, coefficients at 805 nm isobestic wavelength (from Schmitt, 1992 and Steinke, 1987):

Kw=0.0001, Kw is the absorption coefficient of water.

Sw=0 at 805 nm, Sw is the absorption coefficient of water (which is =0).

Kb=1.04*HCT

Ks=0.002

Sb=11*(1−HCT)*(1.4−HCT)*HCT

Ss=0.93

S (Khalil)=forearm=0.7 to 1.1.

All coefficients are in per mm values; see Equation set (28s)-(28j) below for their physical interactions.

The radial "r" values are known from the linear array dimensions, spaced at 1.75 mm in the present embodiment.

B—Measured Parameters:

LOG[(i1−N1)*r1$^2$*R1]: i1, r1, R1 and N1 are defined as follows: the 1, 2, 3 . . . 8 in each case refers to the first . . . through eighth detector (photodiode) position located 1.75 mm from the source 805 nm LED and a 1.75 mm separation from the other photo-detector. Hence, i1 is the measured intensity at position 1, r1 is the radial distance at position 1, at 1.75 mm, R1 is a programmable gain factor for amplifier 1 and N1 is an optical "crosstalk" measured value due to stray or Specular light at position 1. N is measured without any medium present, just in free air. A fiber optic bundle or a clear plastic disposable and their reflectivity can be cancelled knowing their N value also. These same definitions apply to each individual photodiode from position1 to position 8. R (of Equation (24)) is not to be confused with R1 . . . R8 (programmable gain factors).

C—Important photo-optical equation set:

$$S = (Sb - Ss)Xb + SsXw(1 - Xw) \quad \text{Eq. (28a)}$$

$$Sb = H(1 - H)(1.4 - H)11 \quad \text{Eq. (28b)}$$

$$K = (Kb - Ks)Xb + KsXw(1 - Xw) \quad \text{Eq. (28c)}$$

$$Kb = 1.04\ H \quad \text{Eq. (28d)}$$

$$\alpha^2 = 3KS \quad \text{Eq. (28e)}$$

$$\frac{\alpha^2}{3S} = K \quad \text{Eq. (28f)}$$

$$\Delta K = Kb\Delta Xb \quad \text{Eq. (28g)}$$

$$\Delta S = (Sb - SsXw(1 - Xw))\Delta Xb \quad \text{Eq. (28h)}$$

$$\frac{\Delta K}{\Delta S} = \quad \text{Eq. (28i)}$$

-continued $$\frac{Kb}{(Sb - SsXw(1-Xw))} = \frac{1.04\,H}{(H(1-H)(1.4-H)11 - SsXw(1-Xw))}$$

$$Xb = \frac{K}{HCT} \quad \text{Eq. (28j)}$$

Significant assumptions in Equations (28a)-(28j): at 805 nm Ks and Kw are small and can be ignored. H above is HCT.

Figure 13A:
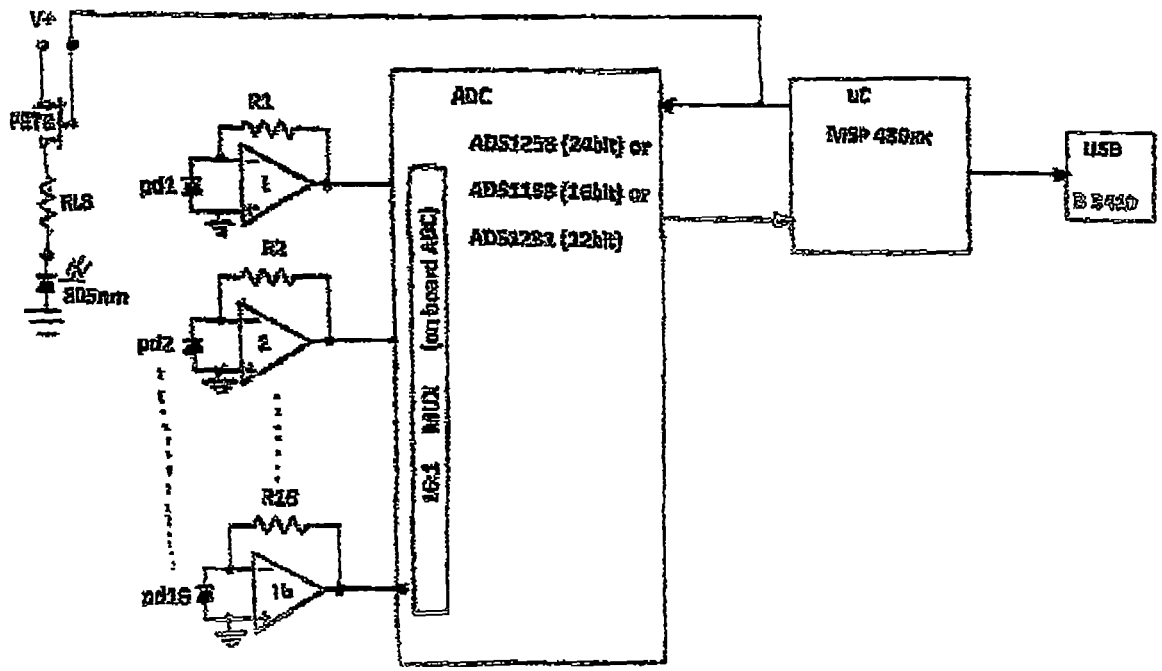
FIG. 13a illustrates a single sensor circuit diagram for a single sensor circuit of the apparatus for data acquisition.

D—Using computer-based programs such as Mathematica 10.0 or computer code embedded in circuits such as those shown in FIGS. 13a and 31b (more specifically, in the microprocessors of the circuits), and since K is not directly measureable, solving for S and $\alpha$, can be accomplished using curve fitting algorithms as described herein.

There are two algorithms using a derivative approach: d(Log[$R^*r^2$])/dr (eliminating the 17.52 (A8, Ao, Rs terms) and all offsets):

1. A one stage algorithm with W=weighting factor={1111111} and
2. A two stage algorithm with W={1000000} where alpha is determined by averaging the last 3 d (Log[$R^*r^2$])/dr values. Using the W values to weight each data point with a one or zero allows for determination of S. These two algorithms of the curve fitter can be used for measurements in conditions of a varying Ss or heavy pigmentation, such as black skin. The preferred embodiment uses measurements which are performed on the fat pad of the fingertip, which avoids the melanin issues, however.

Calluses are likewise a concern because they increase the internal diffuse reflectance, "rd", and decrease Xb or $$Xb = \frac{V\text{blood}}{V\text{blood} + V\text{tissue} + V\text{water} + V\text{callus}}$$

where Vcallus is volume of callus. But the $$\frac{\Delta K}{\Delta S}$$

ratio Equation (28i) cancels out this type of Xb problem. The callus, or epithelial thickening, simply changes the Xb of the homogeneous system, which is cancelled as described in Equations (28a)-28(j). This is the case for most human fingertip conditions. However, many patients may have epithelial thicknesses which may cause a significant index of refraction mismatch. Hence that additional "rd" term of Equation (3b) must be determined or cancelled. One method to eliminate that "rd" term is to determine the radial r where the maximum of the Log[R] versus radial, r occurs. That point is virtually independent of the "rd" effect and serves as a good representation of S. Another method for knowing or eliminating the "rd" term is determining the value of the offset of Log[R] at radial r=0. That value shows a large dependence on the "extrapolated boundary value, "−zb" and hence can eliminate the "rd" effect. Likewise, applying the Robin Boundary Condition as in Equation (19a) will cancel the "rd" terms. Still another method for eliminating "rd" effects is by choosing the R0 value in Equation (19a) in the 4 to 7 mm radial region. The alpha value, alphaRD, determined from (19a) is compared to the alpha value determined by a curve fitter algorithm, alphaCF, (or a simple slope method, alphaAVG). Then any finger to fmger variations due to callus or patients is eliminated with the (alphaCF/alphaRD)$^n$ ratio (or the (alphaCF/alphaAVG)$^n$), where n is determined empirically. In particular, S, in the equations below, will be modified by those alpha ratios.

The third algorithm is the preferred method which is herewith defined as "Full Fit" of Equation (24). First, a straight line fit of the last 4 data point, r5, 6, 7, 8 gives a good estimate of alpha. Secondly, extending that line to r=0, an offset value (Ao) of less than 17.52 (Io) is found. Next, the algorithm increments up in 0.01 units from that "Ao" value until a best S is fitted to the data points. Finally, with the best "incremented Ao" (near to 17.52) and the best S and a values, those values are again fitted one last time (within milliseconds) to the data (to where alphaCF/alphaAVG=1.0+−5% and that last "incremented Ao" is held for the remainder of the data collection) to find the optimum S and $\alpha$. This "incremented Ao" can be called "rastering" and is important because Io, source intensity, itself can have drifting due to LED (light source) heating. Also this "rastering" eliminates black skin or other first layer (Epithelial) variations or inhomogeneities. Hence, "rastering" or "incrementing Ao" deals with the large variations (such as, specular reflections, Rs) that can occur in each patient circumstance.

Yet another method for determining $\alpha$ and S relies on the slopes (determined by radial derivatives, d Log[$R^*r^2$]/dr) but done by the straight line fit of the last 3-4 data points (8 to 14 mm) for $\alpha$ and a straight line fit of the first 2 points (1.75 to 3.5 mm) for S. This S, however has a strong functionality in "rd" and hence needs that "rd" (or Xw) effect cancelled.

One of the advantages of using curve fitting algorithms is that when tissue inhomogeneities are present (or layered tissues) the fitter provides a filtering of the data, i.e., giving smoothed or averaged data values. To further smooth the tissue inhomogeneities, or gradients in Xb, FIGS. 15a, 15b and 16 demonstrate this smoothing (averaging) by illuminating the tissue from opposite directions. Combining those radial reflectances smooths (makes homogeneous) the entire region in Xb, (1−Rs) and Xw. An example of this averaging or combining reflectances is at the same time interval, average the Snear and Sfar together and alphanear and alphafar together. Where "near" is the photodiode nearest to r1 and "far" is closest to r8. Hence, the above mentioned algorithms, especially "rastering A8" and radial slopes, for $\alpha$ and S determinations are more accurate due to improved homogeneity. Finally, an advantage of reversing the photodiode array to an LED array and reflectance measured by only one or two photodiodes is that crosstalk is minimized due to narrow radial illumination patterns of LEDs.

Since alpha, $\alpha$, is a crucial optical parameter, implementing Equation (19a) by curve fitting is useful especially when smoothing the entire tissue region as described above, see FIGS. 15a, 15b and 16, thereby minimizing gradients in Xb. If the tissue regions are not smoothed as described, minimizing Xb gradients, the measurement of K, S, $\alpha$ and their time derivatives may not be meaningful, accurate or existent. Depending on the magnitude of A1 (0<A1<1), the resultant value of Equation (19a) will be an alphaRD with no "rd", A8, intensity variations or even skin color effects.

Likewise, since S is the other crucial parameter to determine for this self-normalizing process, the following non curve fitting method is described. Using the Log[$R^*r^2$] vs r data, the radial derivative is performed on those logarithmic values; the radial value where the derivative is 0 is inversely related to S, called Rat0^−0.25. In other words, it is the radial value of where the maximum Log [R*r$^2$] occurs. This value Rat0$^\wedge$−0.25 is almost independent of "rd" (or Xw).

In summary, because there are three variables with one equation, the above methods, such as rastering A8, Ao, or differentiating the radial data points in r, can eliminate one or another of those variables individually allowing for the solution of α and S.

E—Solve for HCT and Xb with α and S known, the self-normalization methodology:

Knowing the values α and S, the following equations are used to solve for HCT:

$$\text{Solve}\left[\left(\left(\frac{\Delta K}{\Delta S} - \frac{1.04H}{(H(1-H)(1.4-H)11 - SsXw(1-Xw))}\right)\right) == 0, H\right] \quad \text{Eq. (29)}$$

This "Solve" equation (Mathematica 7.0) essentially finds the roots of Equation (29) and will return three possible HCT values because of the third order polynomial nature of the "solve" equation above. Nevertheless, the "solve" equation merely needs to be bracketed in the HCT range because the only meaningful HCT values would be in the following range of values:

0.20<solve equation<0.65.

Figure 12:
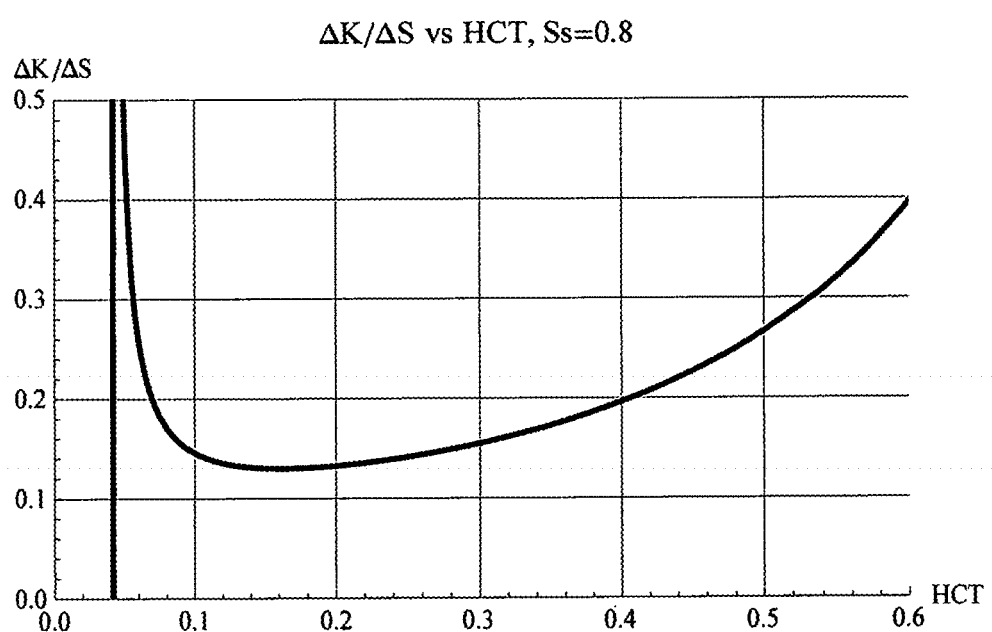
FIG. 12 is a graph of the relationship between HCT and the measured values K and S.

FIG. 12 is a graph illustrating the relationship between HCT and the measured values K and S according to Equation (29).

Or the direct use of Equation (29) as the polynomial itself is:

$HCT = 32.113(FH22^3) - 31.574FH22^2 + 10.909FH22^1 - 0.7659$ Eq. (29a)

where FH22 can equal the measured values of Equations (31) and (32) below.

Now with HCT known, the following equations give Xb:

$$Xb = \frac{K}{HCT}, \text{ where } \frac{a^2}{3S} = K \quad \text{Eq. (30)}$$

It is also clear from the above Equation set (28a)-(28j) that if Ks is small and Ss is a constant, then HCT can also be determined using FIG. 12, Equation (29a) and Equation (31):

$$\frac{K}{S - SsXw(1-Xw)} = \frac{\frac{\alpha^2}{3S}}{S - SsXw(1-Xw)} = FH22. \quad \text{Eq. (31)}$$

This is the completely DC or non-pulsatile solution of HCT. If, on the other hand, K is determined from Equation (19a) with R0 in the 4 to 7 mm range and α as above, then S becomes $$\frac{\alpha^2}{3K}.$$

Equation (31) shows no time derivatives are used, only a radial derivative is required.

Referring to Equations (28g and 28h) changes in Xb, ΔXb, can occur due to changes in pressure (dPress), measurement height (dheight) relative to the heart, venous return (dvenous) to the heart, such as, coughing, or Valsalva maneuvers and not be related in time. Likewise, a change in Xb can occur over time due to normal respirations (over 1-5 second interval), or heartbeats (within a 1 second interval), but whether a change in Xb is over time or due to pressure (dPress), or dheight, or dvenous measuring a difference in intensity (or reflectance) results in:

$$\frac{\Delta K}{\Delta S} = \frac{\left(\frac{a^2}{3S}\right)_1 - \left(\frac{a^2}{3S}\right)_2}{s_1 - s_2} \quad \text{Eq. (32)}$$

Equation (32) is used with FIG. 12 or the solve Equation (29) or (29a) to find HCT as well. This describes both the non-pulsatile (due to physiological changes) and the pulsatile embodiment of the method as well, and can be used in a pulsatile fingertip pulse Oximeter. Recall, as mentioned above, the measurement of dS/dt may not be measured at all radial, r. Indeed, there are specific radial regions which are independent of S or whose sensitivities to S are low, positive, negative or even non-existent (See FIG. 1, Schmitt, 1991, page 1197 and Kumar, 1997, pp 2288-2291) and hence often dS/dt is "neglected". Those tissue regions where S sensitivities are unknown or volatile is a major drawback and minimizes the usefulness of Navon (US 2010/0076281 A1). Hence, stipulating those precise regions of S and dS/dt detection, as discussed herein, is a significant improvement over Navon (US 2010/0076281 A1).

Figure 13B:
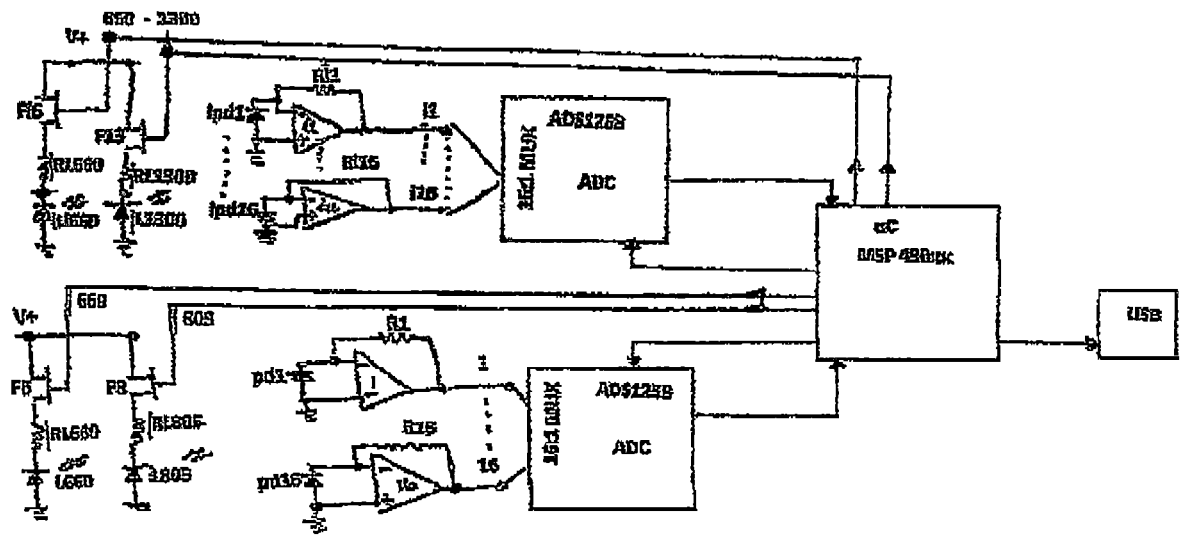
FIG. 13b illustrates multi-sensor circuit diagrams for a multi sensor circuit of the apparatus for data acquisition.
Figure 14:
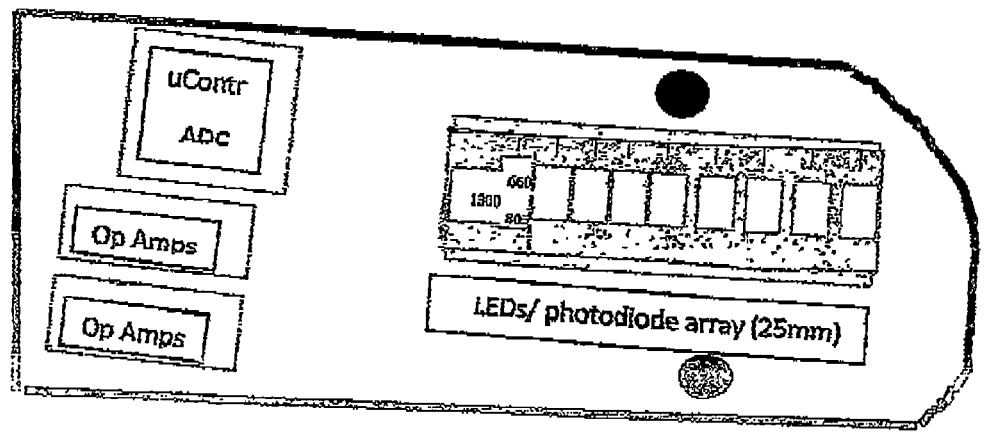
FIG. 14 illustrates the built up printed circuit board and photo-array used in the apparatus according to the invention, and particularly the physical size of the photo-array and alignment of the detectors.

As shown in FIGS. 13a and 13b, the computing mechanisms are applicable to a main frame, PC, smart phone device having the number crunching, memory and processing capabilities of the state of the art. With that computer capability the above determinations can be easily displayed, or transmitted, in real time and continuously if desired.

5—Preferred Apparatus Embodiments

While the preferred embodiment shown in FIGS. 15a and 15b show a linear sensor array of equally spaced photodiodes (with light sources at opposite ends of the linear photodiode array), likewise a circular sensor array or CCD sensor array each maintaining known photo-detector distances from the light source would also meet the requirements of this spatially resolved reflectance method. The requirements would include a multi-element, co-planar array of either photo-detectors or light sources such as LEDs, LDs or fibers situated in a known spatial arrangement, again linear or circular as example. Knowing the spatial arrangement, that is, the radial r separations (r1-8) exactly and the R1-8 gain values exactly and the N1-8 values exactly, the correct S, K determinations can be made first. The photodiode array of the preferred embodiment consists of Silicon Photodiodes. However, when other analytes are also to be determined, InGaAs photodiodes can be included, as shown in FIGS. 15a and 15b.

While not shown in the Figures, an "on-board" photodiode can directly compensate for LED intensity variations can be included on the printed circuit board. A8 (or the source intensity), if not a function of the fluence itself, would be measured and known.

Calibration for the physical embodiments can be done using Intralipid mixtures (described above) or with "False Fingers" made of Epoxy resins (Shore A hardness of 20) mixed with appropriate amounts of 1 micron glass beads and powdered ink dyes.

Figure 16:
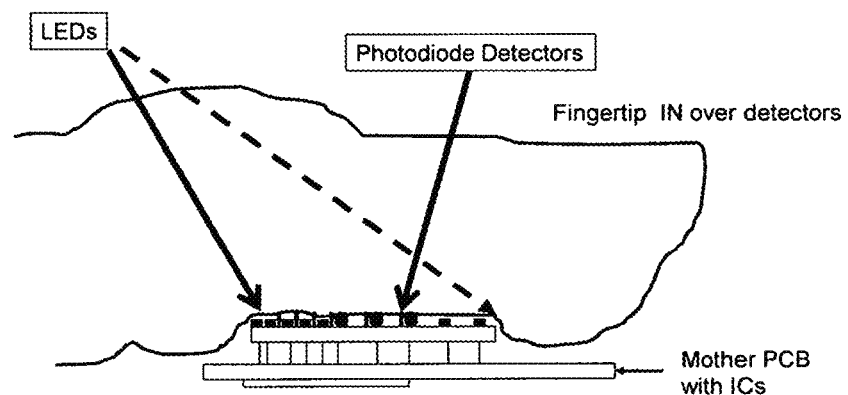
FIG. 16 illustrates the photo-array of the invention with a finger in direct contact therewith and $2^{nd}$ set of 805, 660 nm LEDs.

FIG. 16 shows one such finger arrangement in contact with the photo-array. Solving for Tissue Water, HCT-Independent O2SAT, Glucose (A1C), Other Analytes, Psychotropic Drugs and Chemotherapeutic Agents, Etc An 800 nm wavelength (or other wavelengths described herein) is chosen because it is isobestic for Hemoglobin (HGB). Thus, (a) no additional oxygen saturation measurement is required and (b) no requirement to distinguish two separate Xbs: Xb=Xvenous+Xarterial. Since reduced and oxyhemoglobin have the same extinction coefficient at 800 nm, venous and arterial blood is seen as just one constituent—blood. Other isobestic regions will likewise be important for the measurement of other constituents; one such isobestic wavelength is at 1300 nm. But this region has significant water absorbance and will need to be properly cancelled or known exactly.

Xw, Concentration of Water in the Tissue (1300 nm)

An example of the Xw effect is seen in the following equation:

$$K = Kb\ Xb + Xw\ Kw + (1 - Xb - Xw)\ Kother \qquad \text{Eq. (33a)}$$

where Xw is the fractional water volume per total tissue volume, and Kw is the water absorbance at 1300 nm. These would need to be known in order to determine Kother, if Kother is desired. These water values will be critical because many of the drugs and analytes, etc will have absorbance peaks in a dominant water region.

For this new wavelength, 1300 nm, a new Ss would be determined, since Ss is a function of wavelength:

$$Ss = A\lambda^{-B}$$

In a similar way the HCT and Xb are important for the determination of plasma-dissolved constituents. The HCT value is needed to allow the computation of specific plasma values. An example from (AA) above where Kb contains the xxx desired chemical dissolved in the plasma:

$$Kbxxx = 1.04H + (1-H)\ (Kplasma + Kxxx) \qquad \text{Eq. (33b)}$$

More correctly, $K = \Sigma c_i^* \epsilon_i$ or:

$$Kbxxx = 1.04H + (1-H)\quad (Cpla^* \epsilon_{pla} + Cxxx^* \epsilon_{xxx} + Cyy^* \ldots) \qquad \text{Eq. (33c)}$$

Cpla is the plasma concentration and $\epsilon_{pla}$ is the plasma extinction coefficient. The other constituents, xxx, are then added via the proration of their extinction value times their concentration. Since the plasma extinction value is about the same value as the water value, the measurement of Xw is accomplished with the 1300 nm, as follows:

If HCT and Xb are found as above, then with Sb and Xb known we measure $S_{13}$ and the tissue water content becomes:

$$Xw = \frac{(Sb - Ss)_{13} Xb + Ss_{13} - S_{13}}{Ss_{13}} \qquad \text{Eq. (34)}$$

It is also clear that if 2 wavelengths are used, 800 nm and 1300 nm, the major unknowns of Xb, Xw, Ss and HCT can be determined without a pulsatile blood flow using Equation set(35a)-(35d):

$$S_8 = (Sb_8 - Ss_8) Xb + Ss_8(1-Xw); \qquad \text{Eq. (35a)}$$

$$S_{13} = (Sb_{13} - Ss_{13}) Xb + Ss_{13}(1-Xw); \qquad \text{Eq. (35b)}$$

$$k_8 = (kb_8 - ks_8) Xb + ks_8(1-Xw); \qquad \text{Eq. (35c)}$$

$$k_{13} = (kb_{13} - ks_{13}) Xb + ks_{13}(1-Xw); \qquad \text{Eq. (35d)}$$

Equations (35a)-(35(d) are four equations with five unknowns but either Ss8 or Ss13 is a constant and the S8,13 and K8,13 can be measured now.

The relevance of knowing the tissue water concentration cannot be over stated since patients requiring renal dialysis due to End Stage Renal Disease retain toxic levels of water.

O2SAT (660 nm)—HCT Independent

The choice of other wavelengths coupled with Xb and HCT done at 805 nm will allow the calculation of other blood constituents. As an example, the ratio of 660 nm/805 nm plus HCT results in an HCT—independent, cold hand insensitive, non-pulsatile O2SAT value.

For the non-pulsatile O2SAT:

$$SAT = \frac{\left(\frac{\alpha_6}{\alpha_8}\right)^2 \left(\frac{S_8}{S_6}\right)\sigma_{8or} - kb_{6r}}{(kb_{6o} - kb_{6r})}, \qquad \text{Eq. (36)}$$

where $\frac{S_8}{S_6} = .95$ a constant $$O2SAT = \frac{\left(\frac{K6}{K8}\right)(Xv)*Kb805 - (Xv)*Kv660}{(Xa)*Ka660 - (Xv)*Kv660 + (Xv - Xa)*Kb805*\left(\frac{K6}{K8}\right)} \qquad \text{Eq. (36a)}$$

Hence, 660 nm/805 nm alpha ratios and the S8/S6 ratios are measured, the other values are known, where K6 and K8 can be measured by curve fitting.

AC (pulsatile) measured 02SAT is already determined directly (by standard algorithms) and displayed in this present embodiment since there is already a max and min set of logarithm{intensity} values determined for each pulse.

Using 1300 nm for water, 1900 nm, 950 nm, 1050 nm for glucose determination, and other specific spectral peaks or valleys for the drugs and chemotherapeutic agents of interest, those blood and plasma parameters can also be calculated. Indeed, for some desired constituents knowing the Ks and Ss at those wavelengths may be required.

While the present embodiment utilizes eight photodiodes equally spaced, it should be clear that with the final known coefficients, Equation (24) would only require at minimum two measured points, one known spatial measurement in the 0 to 5 mm region and one in the 10 to 14 mm region. Likewise, it is clear that a single LED (800 nm) and a single photodiode, which can be physically moved to known radial values, would satisfy the requirements of Equation (24) also allowing for the HCT determinations as above. It should also be clear that the equations mentioned also allow for the HCT determination transmissively through the tissue knowing the tissue thicknesses (d) or distances from the emitter and each detector.

Since the relationship between HCT and HGB is well known (MCHC, the mean cell Hemoglobin concentration, is typically 0.33), the present invention anticipates the display of HGB concentrations as well.

Since S, K, and $\alpha$ are fundamental optical parameters measured by this methodology for medical diagnostics or monitoring, other areas of use of this technology are anticipated. For example, it may be used in measuring the fat content in milk, in real time, as a cow is being milked and even in refurbishing motor oils. The Intralipid used in the present invention is a fat emulsion; hence milk fat or oil concentrations are easy determined. Indeed, any semi-liquid which is not a pure solution but having scattering elements is contemplated with this technique.

Even though the apparatus in accordance with the present invention will measure and monitor HCT as one of the constituents, it is primarily intended as an Xb monitor.

In order to measure the HCT noninvasively, it is necessary to measure the Xb also. These two parameters, HCT and Xb, are interlocked or multiplied together as Xb*HCT.

The Xb parameter is NOT reported or measured anywhere, BUT Xb is overwhelmingly important because without knowing the Xb, it is not possible to know the amount of, for example, glucose within the blood, but only to know the amount of glucose in the entire finger. To doctors, it does not matter how much glucose is in the entire finger; it only matter how much glucose is in the blood itself.

So Xb is overwhelmingly important because to know the value of any constituent of the blood it is necessary have to know where the constituent (glucose or drug) is. Is the measurement done in the blood or in the tissue spaces?

To summarize, the purpose of the method in accordance with the invention is to perform a "self-normalization" (as described in the paragraphs under the headings "Relationship of alpha and S" and "Relationship of K and S"). ONCE alpha and S are found (using only one wavelength, hence the term "self-normalization"), the ratio of K/S cancels out (or parametrically eliminates) Xb, leaving the desired HCT.

The steps for determining alpha, K and S are described in the paragraphs under the heading "To solve for $\alpha$, S, using only one isobestic wavelength, DC measurements and Equation (24)." These steps employ computer-implemented algorithms that determine the best curve fit or slopes from which the alpha, K and S are found.

Section D under heading "To solve for $\alpha$, S, using only one isobestic wavelength, DC measurements and Equation (24)" explains that "rd" (Xw) and (1-Rs) may have to be removed and how to do so with those alphaCF/alphaRD ratios, and radial derivatives of Log [R*r²] etc.; and also explains a computer-implemented "rastering" method for eliminating skin color and other Io, Ao, absolute intensity effects. Likewise, the amount of "rastering of Ao" is proportional to the Xw and gives the offset term in the denominator of Equation (31).

Section E under the heading "To solve for $\alpha$, S, using only one isobestic wavelength, DC measurements and Equation (24)" describes crucial computer-implemented manipulations necessary for the actual "self-normalization."

The first paragraph under the heading "5-Preferred apparatus embodiments" explains that known spatial arrangement is crucial, because knowing the radial, r, separations (r1-8) exactly and the R1-8 gain values exactly and the N1-8 values exactly, the correct S, K determinations can be made first.

Thus, first, alpha and S are determined by slope, or using any of three curve fitting algorithms discussed in Section D under the heading "To solve for $\alpha$, S, using only one isobestic wavelength, DC measurements and Equation (24)."

Once alpha and S are known, the next step is to find $\Delta K/\Delta S$ using Equation (29) OR to find FH22 using Equation (29a). Eq. (29) returns three possible HCT values, and Eq. (29a) also solves for HCT.

Equation (30) then uses the measured value of K and the calculated value of HCT to give Xb.

Equation (31) uses the measured values of K and S (and also alpha) to give FH22, which can then be used in Equation (29a) to solve for HCT.

Alternatively, the values for alpha and S (at Xb_condition 1 and Xb_condition 2) can be used in Equation (32) to give $\Delta K/\Delta S$, which can then be used with Equation (29) to solve for HCT or with Equation (29a) (in conjunction with Equation (31)) to solve for HCT.

In other words, we can use $\Delta K/\Delta S$ to find HCT, and we can also find $\Delta K/\Delta S$, or HCT, by using FH22. Note that HCT/0.34 is about equal to Hemoglobin.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described. Specifically, these above teachings relate in large part to reflective, DC, non-pulsatile determinations. Further variations and mathematical functions described below relate to light transmission, AC, pulsatile determinations.

Beginning with the transmissive equation, utilizing the k3 modified spherical Bessel function, where transmission=i (intensity of light) and other terms defined as noted above, either at approximately 660 nm, 800 nm or 1300 nm:

$$\text{Log}(i8) = A8 + \text{Log}\left[\left(\frac{S}{(S+K)^1}\right)^1 \left(1\left(\frac{1}{1-e^{-2*\alpha*d}}\right)^1 * k3\right)\right] \quad \text{Eq. (37)}$$

$$dii = \left[\frac{dLnR*r^2}{da}\frac{d\alpha}{dxb} + \frac{dLnR*r^2}{dS}\frac{dS}{dxb}\right] * Xb' \quad \text{Eq. (38)}$$

$$\text{where: } Xb' = \frac{dxb}{dt} \quad \text{Eq. (39)}$$

Where: $PL = $ $$\frac{dLnR*r^2}{d\alpha} \text{ and } \frac{d\alpha}{dxb} = \frac{3S8}{2\alpha}\left(\Delta K + K * \frac{\Delta S}{S}\right) \text{ and } \Delta S = (Sb - Ss)$$

$$dii = \left[PL * \frac{3S}{2\alpha}\left(\Delta K + K * \frac{\Delta S}{S}\right) + \frac{dLnR*r^2}{dS}\frac{dS}{dxb}\right] * Xb' \quad \text{Eq. (40)}$$

Where: $\frac{dLnR*r^2}{dS}\frac{dS}{dxb} * XB' = PLSdx = dS' \quad \text{Eq. (41)}$ $$dii - dS' = PL * \frac{3S}{2\alpha}\left(\Delta K + K * \frac{\Delta S}{S}\right) * Xb', \quad \text{Eq. (42)}$$

where $-dS'$ is crucial at long wavelengths.

$$\frac{dii - dS'}{PL} = \frac{3S}{2\alpha}\left(\Delta K + K * \frac{\Delta S}{S}\right) * Xb' \quad \text{Eq. (43)}$$

$$\Delta\alpha 8 = \frac{d\alpha 8}{dxb} = \frac{3S}{2\alpha 8}\left(\Delta K 8 + K 8 * \frac{\Delta S 8}{S 8}\right) * Xb' = \frac{dii8 - dS8'}{PL8} \quad \text{Eq. (44)}$$

$$HCT = \frac{\Delta\alpha 8}{xb13} * \frac{2*\alpha 8}{S8} - \Delta S8\left(\frac{\alpha 8}{S8}\right)^2 \text{ and/or} \quad \text{Eq. (45)}$$

$$HCT = \frac{\left(\frac{dii8 - dS8'}{PL8}\right)}{xb13'} * \frac{2*\alpha 8}{S8} - \Delta S8\left(\frac{\alpha 8}{S8}\right)^2$$

$$XB13' = \frac{dii13 * S13}{\Delta S13\left(PL13 * \frac{\alpha 13}{2} + \frac{-2*K13}{(S13+K13)}\right)} = Xb', \quad \text{Eq. (46)}$$

using a 1300 nm LED source $$R138M = \frac{\left(dii13 - Xb'\frac{PL13Sdx}{\Delta SS13}\right)}{\left(dii8 - Xb'\frac{PL8Sdx}{1.69}\right)} * \frac{PL8}{PL13}\frac{\alpha 13 * S8}{\alpha 8 * S13} \quad \text{Eq. (47)}$$

$$HCT(xw) = \frac{kw13\left(3 - 3Xw\left(1\frac{\Delta S13}{S13}\right)\right)}{R138(1.04) + kw13} \quad \text{Eq. (48)}$$

-continued $$Xw = \frac{1 - \frac{HCT*(R138(1.04) + kw13)}{3*kw13}}{\left(1 - \frac{\Delta S13}{S13}\right)},$$ Eq. (49)

note HCT of Eq. (45) is used

The "d" is either fixed or $d(i13) =$ Eq. (50)

$$(-1.5587*(\max i13*1.2*\alpha 8^{.10}) + 27.55)^1$$

As mentioned earlier, the PL is a function of "d or d(i13)" and required to normalize equations 43, 46 and 47.

As taught by Schmitt (U.S. Pat. No. 6,606,509 B2) the dii13 would be a very low level signal with poor signal to noise in the 1300 nm wavelength region due to water absorption. Therefore according to (U.S. Pat. No. 6,606, 509 B2), an occlusive device is required to amplify and augment the 1300 nm signal strength. However, this occlusion requirement is obviated and avoided entirely in this specification since a photodiode (InGaAs) can achieve a large signal gain with minimal noise gain through an NPN transistor being added, greatly enhancing the 1300 nm signal, dii13, above the noise.

These unique transmission teachings and mathematical functions are not only appreciated by those skilled in the art but constitute the following claim language.

APPENDIX

Detailed Mathematics

If the simple LED approach and profiles (point source) are altered then the following convolution math should be re-incorporated to account for different Source Profiles:

$\psi = f(\rho, \theta, \phi)$ $\phi$ is the Azimuthal dependence, seen in $\text{Cos}[m\phi] = e^{im\phi}$, when m=0, $\text{Cos}[m\phi]=1$, meaning azimuthal independence, because of axial symmetry, pp 759-60, all points in the x, y plane would have the same $\psi$ at the same radius, r, from the origin m is the separation constant used for the azimuthal component of a solution to the differential equation, pp 558-60, $\psi = R(\rho)\theta(\theta)\Phi(\phi)$ $\int_0^\infty \text{Sin}[\alpha z] d\alpha$ as $e^{\alpha z}$ and $Q_m$ all divergent terms which are ecluded, pp 560, 602, 759-60, the boundary conditions requeire conergence, as do the $P_n$ (Cos $\theta$) Legender Polynomials and $\int_0^\infty \text{Cos}[\alpha x] d\alpha$ Prahl did his thesis considering Gaussian Profiles but convoluting with a cylindrical source function, not Gaussian function, showed greater accuracy. Must use at least a 2nd order Bessel function and must use a Green's function in the convolution $$\psi = -\frac{1}{D}\left(\int_{Vol} G*PoFo\, dV + \int_{Sur,z=d} G*QdS - \int_{Sur,z=0} G*QdS\right)$$

$$\psi = -\frac{1}{D}\int_{Vol} G*SdV,$$

$G = G(\rho, t),$ $S = S(t),$ $dV = 4\pi t^2 dt,$ $$\int_V dV = \iiint,$$

see pp 600, 609 showing the multipole (source) expansion or convolution

If cylindrical coordinates are used— keep the $K_n$ terms and the $\text{Cos}[\alpha z]$ term (not the divergent $\text{Sin}[\alpha z]$) and use the Fourier transforms:

$$\frac{1}{\sqrt{\rho^2 + z^2}} = \frac{2}{\pi}\int_0^\infty K_0 \text{Cos}[\alpha z] d\alpha \text{ and}$$

$$\frac{r}{(\rho^2 + z^2)^3} = \frac{2}{\pi}\int_0^\infty K_1 \text{Cos}[\alpha z] d\alpha,$$

see pp 602, 609, 778, 931, and 944

In cylindrical $$\psi = \frac{1}{\rho}[I_0 K_0] + \frac{r}{\rho^3}[I_1 K_1],$$

where: $I_n K_n$ are not closed form Bessel functions we approximate the as:

$$I_0 = \frac{e^{\alpha r}}{\sqrt{\alpha r}},$$

$$K_0 = \frac{e^{\alpha r}}{\sqrt{\alpha r}},$$

$$I_1 = \frac{i_1}{(\alpha r)^{1.5}},$$

$$K_1 = \frac{k_1}{(\alpha r)^{1.5}}$$

If spherical coordinates, Green's functions, and by analogy the Electrostatic or Magnetic state models (see pp 742, 761, 778, 782) and Legender Polynomials, $P_n \text{Cos}[\theta]$, are used to describe the $\theta$ dendence, then the photon density is:

$$\psi = \alpha\left[\sum_n^\infty [i_n k_n] \sum_n^\infty \left(\frac{r}{\rho}\right)^n P_n \text{Cos}[\theta] \int S(\rho) dV\right]$$

see pg 609, $s(\rho) = Fo = e^{-\eta \rho}$, where empirically $$\eta = \frac{1}{2 \text{ mm}} \text{ and } S = S_0 e^{-\eta \rho},$$

$$s_0 = \frac{2 \text{ Power}}{\pi R^2},$$

where R=radius of the source beam,
see Prahl

The Electrostatic and Magnetic model can take the following forms:

$$\left(\frac{r}{\rho}\right)^n \text{ or } \left(\frac{r^n}{\rho^{n+1}}\right) \text{ or } \left(\frac{r^{n+1}}{\rho^{n+2}}\right) * P_n \text{Cos}[\theta]$$

see pg 782 and 742 gives the definition of the Legender Polynomial as $$\sum_n^\infty \left(\frac{r^n}{\rho^{n+1}}\right) * P_n \text{Cos}[\theta],$$

also recall that the derivative of one mulitpole leads to another higher multipole—pg 755

Now using the equion in 609 and Spherical Harmonics:

$$\psi = \alpha\left[\sum_n^\infty [i_n k_n] \sum_n^\infty Y_1(\theta_1, \phi_1) Y_1(\theta_2, \phi_2) \int s(\rho) dv\right],$$

but recall m=0,
$e^{im\phi}=1$, or there is no $\phi$ dependence, $$\psi = \alpha\left[\sum_n^\infty [i_n k_n] Y_1(\theta_1, \phi_1) \int s(t) i(t) k(t) t^2 dt * Y_1(\theta_2, \phi_2)\right] * \text{Cos}[m\phi] d\phi$$

Now we take only the first two modified Spherical Bessel terms, n=0, n−1, due to the inability to integrate in the convoltion the higher terms without engendering imaginary terms,
hence using n=0

$$\psi_0 = \alpha[k_0] Y_1(\theta_1, \phi_1) \int_0^\rho i_0(t) e^{-\eta t^2} dt \int_0^\pi \text{Cos}[\theta_2] \text{Sin}[\theta_2] d\theta_2 + \alpha[i_0] Y_1(\theta_1, \phi_1) \int_\rho^\infty k_0(t) e^{-\eta t^2} dt \int_0^\pi \text{Cos}[\theta_2] \text{Sin}[\theta_2] d\theta_2]$$

And using n=1

$$\psi_1 = \alpha[k_1] Y_1(\theta_1, \phi_1) \int_0^\rho i_1(t) e^{-\eta t^2} dt \int_0^\pi \text{Cos}[\theta_2]\text{Sin}[\theta_2] d\theta_2 + \alpha[i_1] Y_1(\theta_1, \phi_1) \int_\rho^\infty k_1(t) e^{-\eta t^2} dt \int_0^\pi \text{Cos}[\theta_2]\text{Sin}[\theta_2] d\theta_2 \text{ or}$$

$$\psi_1 = \alpha[k_1] \frac{3\text{Cos}[\theta_1]}{4\pi} \int_0^\rho i_1(t) e^{-\eta t^2} dt \int_0^\pi \text{Cos}[\theta_2]\text{Sin}[\theta_2] d\theta_2 + \alpha[i_1] \frac{3\text{Cos}[\theta_1]}{4\pi} \int_\rho^\infty k_1(t) e^{-\eta t^2} dt \int_0^\pi \text{Cos}[\theta_2]\text{Sin}[\theta_2] d\theta_2 \text{ or}$$

$$\psi_1 = \alpha[k_1] \frac{3\text{Cos}[\theta_1]}{4\pi} \int_0^\rho i_1(t) e^{-\eta t^2} dt \frac{1}{2} + \alpha[i_1] \frac{3\text{Cos}[\theta_1]}{4\pi} \int_\rho^\infty k_1(t) e^{-\eta t^2} dt \frac{1}{2}$$

and now where $\text{Cos}[\theta_1] = \frac{r}{\rho}$ $$\psi_0 = \alpha[k_0] \int_0^\rho i_0(t) e^{-\eta t^2} dt + \alpha[i_0] \int_\rho^\infty k_0(t) e^{-\eta t^2} dt$$

$$\psi_1 = \alpha[k_1] \frac{3r}{24\pi\rho} \int_0^\rho i_1(t) e^{-\eta t^2} dt + \alpha[i_1] \frac{3r}{24\pi\rho} \int_\rho^\infty k_1(t) e^{-\eta t^2} dt$$

and this is equal to:

$$\psi = \alpha\left[\frac{i_0 k_0}{\alpha\rho}\right] + \alpha\left[\frac{i_1 k_1}{(\alpha\rho)^2}\left(\frac{3r}{2\rho}\right)\right]$$

Or using Legender Polynomials representing the Spherical Harmonics:

$$\psi = \alpha\left[\sum_n^\infty [i_n k_n] \int s(\eta t) i(t) k(t) t^2 dt * \left(\frac{r^n}{\rho^n}\right) * P_n \text{Cos}[\theta] * \text{Cos}[m\phi] d\phi\right]$$

gives:

$$\psi = \left[\frac{i_0 k_0 s}{\rho}\right] + \alpha\left[\frac{i_1 k_1 s}{(\alpha\rho)^2}\left(\frac{3r}{2\rho}\right) \text{Cos}[\theta_1]\right]$$

and it becomes $$\psi = \left[\frac{i_0 k_0 S}{\rho}\right] + \alpha\left[\frac{i_1 k_1 S}{(\alpha\rho)^2}\left(\frac{3r}{2\rho}\right)\left(\frac{r}{\rho}\right)\right]$$

see pg 788 for the transform between Spherical Harmonics and Legender polynomials
Finally,
since our sensor arrangement is only viewing a cylindrical or hemisperhical region we can take the hemispherical solutinof the spherical as $$Hemi = -\frac{2}{\rho}\frac{\partial \psi}{\partial \rho}$$

note how the hemispherical solutin and cylindrical look alike $$\left(\frac{1}{\rho^2}\lambda + \frac{r}{\rho^3}X\right)_{hemi} \text{ and } \left(\frac{1}{\rho^{1.5}}\lambda + \frac{r}{\rho^{2.5}}X\right)_{cylindrical}$$

See the Heat transfer equation pp 616-17 in cylindrical coordinates $$\psi = A\frac{e^{-\frac{r^2}{4D^2}}}{r}$$

and in our case becomes $$\psi = \frac{.25}{\mu}\frac{e^{-\frac{Sr^2}{4}+\frac{a^2}{3S}}}{r} + \psi_{Hemi}$$

$$\gamma = 3; \mu = \frac{\gamma}{y^1}; \eta = .76y$$

$\log r 2Rx = 15.75 + 2\text{Log}[r] +$

-continued $$Log\left[\left(\frac{15}{r^2}y^4 e^{.5\frac{x^2}{3y}}\right)\left(e^{-\left(y\frac{r^2}{16}\right)}\right) + ((yy)^1 C5(z\eta hemicylsph + z\eta hemisphi1k1))\right]$$

$$yp1dimcylinderwithz = \left(\frac{3y}{1}xx\right)^1$$

$$\left(\left(\frac{e^{-x\sqrt{r^2+(z-\mu)^2}}}{x\sqrt{r^2+(z-\mu)^2}}\right)^1\left(\left(\frac{e^{-\eta\xi}(e^{\eta\xi}+e^{x\xi}(-1+x\xi-\eta\xi))}{x(x-\eta)^2}\right)^n\right)\right)+$$

$$\chi\left(\frac{e^{x\sqrt{r^2+(z-\mu)^2}}}{x\left(\sqrt{r^2+(z-\mu)^2}\right)}\right)^1\left(\left(\frac{-e^{-b(x+\eta)}(1+b(x+\eta))+e^{-(x+\eta)\xi}(1+(x+\eta)\xi)}{x(x+\eta)^2}\right)^n\right)$$

$$ypcylsphi1k1withz =$$

$$\frac{3yx^2}{\sqrt{r^2+(z-\mu)^2}}xx\left(\frac{e^{-x\sqrt{r^2+(z-\mu)^2}}}{\left(x\sqrt{r^2+(z-\mu)^2}\right)^2}\left(x\sqrt{r^2+(z-\mu)^2}+1\right)\right.$$

$$\left(\left(\frac{e^{-\eta\xi}(2e^{\eta\xi}x^3 + x(-\eta^3\xi+x^2(-2+\eta\xi))}{Cosh[x\xi] + (\eta^3+x^4\xi-x^2\eta(3+\eta\xi))Sinh[x\xi])}\right)^n\right)+$$

$$\chi\left(\frac{x\sqrt{r^2+(z-\mu)^2}Cosh\left[x\sqrt{r^2+(z-\mu)^2}\right]-}{Sinh\left[x\sqrt{r^2+(z-\mu)^2}\right]}\right)$$

$$\left(\left(\frac{e^{-(x+\eta)(b+\xi)}\left(-e^{(x+\eta)\xi}(\eta+x(2+b(x+\eta)))+\right.}{e^{b(x+\eta)}(2x+\eta+x(x+\eta)\xi))}\right)^n\right)$$

If the io or i1 Bessel terms are included, then $$\frac{1}{1-e^{2\alpha d}}$$

is the A or C coefficient in Equation (9) above to give the appropriate negation of the io and i1 terms (and keep the mathematics from "blowing up", i.e. not meeting real world boundary conditions).

If there is a $2^{nd}$ layer problem, i.e., the tissue space is not homogeneous, then including an additional term with the ko or k1 terms corrects for this, the fluence part of that $1^{st}$ layer is added:

$$\frac{e^{-\beta\sqrt{r^2+(z-\mu)^2}}}{\sqrt{r^2+(z-\mu)^2}}.$$

LED patterns vary greatly and can be modeled well, as an example: use Gaussian math, $$\frac{e^{-\beta(r^2+(z-\mu)^2)}}{r^2+(z-\mu)^2}$$

with $$\frac{\partial k1}{\partial z},$$

which models "a peep hole" or very narrow beam, or fiber optic, whereas using Cylindrical math, $$\frac{e^{-\beta\sqrt{r^2+(z-\mu)^2}}}{\sqrt{r^2+(z-\mu)^2}}$$

with $$\frac{\partial k0}{\partial z},$$

models an LED spread out function in radial r.

BIBLIOGRAPHY

1. T O McBride, et al. "Spectroscopic diffuse optical tomography" *Appl. Opt.* 38, 5480, 1999
2. S Fantini, et al. "Absorption spectra of chromophores" *Appl. Opt.* 33, 5204, 1994
3. A Kienle, et al. "Noninvasive optical properties" *Appl. Opt.* 37, 779, 1998
4. L V Wang, et al. "Absorption distribution of optical beam." *Appl. Opt.* 38, 4951, 1999
5. U S Sathyam, et al. "Optical coherence of analytes." *Appl. Opt.* 38, 2097, 1999
6. A Kienle, et al. "Spatially resolved diffuse reflectance." *Appl. Opt.* 35, 2304, 1996
7. T J Farrell, et al. "Tissue optical properties." *Appl. Opt.* 37, 1958, 1998
8. Y Painchaud, et al. "Dual spatial integration." *Appl. Opt.* 39, 4730, 2000
9. G Alexandrakis, et al. "Photon migration." *Appl. Opt.* 39, 2235, 2000
10. A Kienle, et al. "Time-resolved reflectance." *Appl. Opt.* 37, 6852, 1998
11. Y Painchaud, et al. "Optical imaging." *Appl. Opt.* 38, 3686, 1999
12. M Morin, et al. "Time-resolved transmittance." *Appl. Opt.* 39, 2840, 2000
13. SJ Matcher, et al. "Tissue scattering coefficients." *Appl. Opt.* 36, 386, 1997
14. A Kienle, et al. "Veins blue." *Appl. Opt.* 35, 1151, 1996
15. F Bevilacqua, et al. "In vivo tissue optical properties." *Appl. Opt.* 38, 4939, 1999
16. N Iftimia, et al. "Direct-current measurements." *Appl. Opt.* 39, 5256, 2000
17. G Marquez, et al. "Anisotropy in absorption." *Appl. Opt.* 37, 798, 1998
18. A M Helwig, et al. "Glucose and urea." *Appl. Opt.* 39, 4715, 2000
19. M J Hayes, et al. "Artifact reduction" *Appl. Opt.* 37, 7437, 1998
20. J R Mourant et al. "Scattering and Absorptions in phantoms." *Appl. Opt.* 36, 949, 1997
21. L O Svaasnad, et al. "Reflectance measurements of layered media." *Phys. Med. Biol.* 44, 801, 1999

22. RMP Doornbos, et al. "Absolute chromophore concentrations." *Phys. Med. Biol.* 44, 967, 1999
23. A Kienle, et al. "Optics of muscle." *Phys. Med. Biol.* 44, 2689, 1999
24. G Yao, et al. "Optical coherence tomography." *Phys. Med. Biol.* 44, 2307, 1999
25. D L Conover, et al. "Near infrared spectroscopy." *Phys. Med. Biol.* 45, 2685, 2000
26. M Canpolat, et al. "Light transport through tissue." *Phys. Med. Biol.* 45, 1127, 2000
27. R J Gaudette, et al. "Diffuse optical tomographic imaging." *Phys. Med. Biol.* 45, 1051, 2000
28. G Kumar, et al. "Spectroscopy of biological tissue." *Appl. Opt.* 36, 2286, 1997
29. J R Mourant, et al. "Absorption coefficients of highly scattering media." *Appl. Opt.* 36, 5655, 1997
30. R A J Groenhuis, et al. "Scattering and Absorption of turbid materials." *Appl. Opt.* 22, 2456, 1983
31. J S Dam, et al. "Tissue optical properties from diffuse reflectance." *Appl. Opt.* 37, 772, 1998
32. R Bays, et al. "Tissue optical properties by reflectometry." *Appl. Opt.* 35, 1756, 1996
33. Barnett, Alex. "A fast numerical method for time-resolved photon diffusion in general stratified turbid media." *Jr of Computational Physics* 201:771-797, 2004
34. Khalil, Omar S., et.al. U.S. Pat. No. 6,662,031.
35. Steuer, Robert R., et.al. U.S. Pat. Nos. 6,181,958, 6,671,528, 6,873,865.
36. Allen, V. et al., "The modified diffusion dipole model." *Phys Med Biol.,* 1991, 36(12): 1621-1638.
37. Schmitt, J. M., "Simple photon diffusion analysis of the effects of multiple scattering on pulse oximetry." *IEEE Trans Biomed Eng.,* 38: 1194-1203, 1991.
38. Schmitt, J. M. et al., "Multiplayer model of photon diffusion in skin." *J Opt Soc. Am A* 7(11): 2142-2153, 1990.
39. *Mathematical Methods for Physicists,* Arfken & Weber, 6th Ed, ELSEVIER Academic Press, 2005.
40. *Partial Differential Equations for Scientists and Engineers,* Stanley J. Farlow, Dover Publications, 1993, pp 58-60.
41. *Handbook of Differential Equations,* Daniel Zwillinger, 3rd Ed, ELSEVIER Academic Press, 1998, pp 157, 276.
42. Prahl, S. A., "LIGHT TRANSPORT IN TISSUE," Ph.D. thesis, University of Texas at Austin, 1988 (http://oml-c.ogi.edu/~prahl/pubs/pdf/prahl88.pdf).
43. Hielscher, A. H. et al, "Comparison of finite-difference transport and . . . " *Phys. Med. Biol.* 43(1998): 1285-1302.

What is claimed is:

1. Apparatus for non-invasively detecting at least a first constituent in a fluid while contained within tissue, the apparatus comprising:
a photo-array including at least a first photo-emitter and at least first and second photo-detectors, wherein the first photo-emitter propagates a first set of photons in the tissue at a single, isobestic, first wavelength, and the at least first and second photo-detectors detect the first set of photons following propagation into the fluid and emit signals in response thereto, and wherein the at least first photo-emitter and the at least first and second photo-detectors are in a known spatial arrangement; and
a processor operatively connected to the at least first and second photo-detectors for receiving the signals therefrom, for determining the scattering coefficient (S) of the first set of photons in the fluid based on the first set of photons detected by the photo-detectors, and for determining the attenuation coefficient ($\alpha$) of the first set of photons detected by the photo-detectors, for determining an amount of a first constituent in the fluid based on the attenuation and scattering coefficients determined for the first set of photons and determining fractional volume of fluid per total tissue volume (Xb) and determining tissue water fraction (Xw).

2. The apparatus of claim 1, wherein the single, isobestic, first wavelength is selected from the group consisting of: about 800 nm, about 1300 nm, between about 420 nm and about 450 nm, and between about 510 nm and about 590 nm.

3. The apparatus of claim 1, wherein the processor determines from the combination of the scattering coefficient and the attenuation coefficient the absorbance coefficient from photons reflected from the tissue and fluid with no regard to variations in time.

4. The apparatus of claim 1, wherein the at least first photo-emitter and the at least first and second photo-detectors are co-planar and wherein Xb and Hematocrit or RAO are known, for determining the Xw, tissue water fraction.

5. The apparatus of claim 1, wherein the processor determines the scattering coefficient and the absorbance coefficient independently, carries out a "self-normalization" by combining the scattering coefficient and the absorbance coefficient, and uses the combination of the absorbance and scattering coefficients to eliminate the determinable fractional volume of fluid per total tissue volume (Xb) where this Xb elimination is enhanced by combining at least two photo-emitters which illuminate tissue from opposite co-planar directions to "normalize" the tissue homogeneity.

6. The apparatus of claim 1, wherein the first constituent is Hematocrit, the processor determines the scattering coefficient and the absorbance coefficient independently, carries out a "self-normalization" by combining the scattering coefficient and the absorbance coefficient, uses the combination of the absorbance and scattering coefficients to eliminate the fractional volume of fluid per total tissue volume first, leaving the Hematocrit, and then using the Hematocrit to determine fractional volume of fluid per total tissue volume (Xb), each combined to determine the tissue water fraction (Xw).

7. The apparatus of claim 1, wherein: the photo-array further includes at least a second photo-emitter for propagating a second set of photons in the tissue at a second wavelength, the at least first and second photo-detectors also detect the second set of photons following propagation into the fluid; and the processor further determines the scattering coefficient (S) of the second set of photons in the fluid based on the second set of photons detected by the photo-detectors, determines the attenuation coefficient ($\alpha$) of the second set of photons detected by the photo-detectors, and determines an amount of a second constituent in the fluid for a determinable fractional volume of fluid per total tissue volume based on the attenuation and scattering coefficients determined for the second set of photons.

8. The apparatus of claim 7, wherein the second wavelength is a non isobestic, second wavelength, of approximately 660 nm or approximately 970nm where this second wavelength in combination with the first isobestic wavelength determine the $\alpha 1800$ (K8) and $\alpha 660$ (K6) values combined with the S800 and S660 values given as $$O2SAT = \frac{\left(\frac{K6}{K8}\right)(Xv)^* Kb805 - (Xv) * Kv660}{(Xa)^* Ka660 - (Xv) * Kv660 + (Xv - Xa) * Kb805^* \left(\frac{K6}{K8}\right)}$$

where this determines the second constituent: a non-pulsatile, non-time-dependent, reflective Oxygen Sathration measurement.

9. A method for non-invasively detecting at least a first constituent in blood while contained within animal body tissue comprising the steps of:
propagating at least a first set of photons in the tissue for transmission through or reflection by the blood and animal body tissue, wherein the first set of photons is propagated by the at least first photo-emitter at a single, isobestic, first wavelength;
detecting the transmitted or reflected photons using the at least first and second photo-detectors; and
using a processor, determining the scattering coefficient (S) of the first set of photons in the fluid based on the first set of photons detected by the photo-detectors, and determining the attenuation coefficient ($\alpha$) of the first set of photons detected by the photo-detectors, for determining an amount of a first constituent in the fluid based on the attenuation and scattering coefficients determined for the first set of photons and determining fractional volume of fluid per total tissue volume (Xb) and determining tissue water fraction (Xw).

10. The method of claim 9, wherein the tissue is animal body tissue, the fluid is blood, and the first constituent is Hematocrit.

11. The method of claim 9, wherein the amount of Hematocrit is determined by eliminating fractional volume of blood per total tissue volume as a factor for determining the amount of Hematocrit by independently measuring the scattering coefficient and attenuation coefficient and combining the absorbance, scattering, and attenuation coefficients to normalize the fractional volume of blood per total tissue volume.

12. The method of claim 9, wherein the amount of Hematocrit is determined by eliminating the time derivative of the fractional volume of blood per total tissue volume as a factor for determining the amount of Hematocrit by independently measuring the scattering coefficient and attenuation coefficient and combining the absorbance, scattering, and attenuation coefficients given by $$XB13' = \frac{dii13 * S13}{\Delta S13 \left( PL13 * \frac{\alpha 13}{2} + \frac{-2 * K13}{(S13+K13)} \right)} = Xb'$$

normalizing the time derivative of the fractional volume of blood per total tissue volume (Xb').

13. The method of claim 9, wherein the single, isobestic, first wavelength is selected from the group consisting of: about 800 nm, about 1300 nm, between about 420 nm and about 450 nm, and between about 510 nm and about 590 nm.

14. The method of claim 9, wherein: the photo-array and transmissive array further includes at least a second photo-emitter propagating a second set of photons in the tissue at a second wavelength, the at least first and second photo-detectors also detecting the second set of photons following propagation into the fluid; and the processor further determining the scattering coefficient (S) of the second set of photons in the fluid based on the second set of photons detected by the photo-detectors, determines the attenuation coefficient ($\alpha$) of the second set of photons detected by the photo-detectors, and determines an amount of a second constituent in the fluid for a determinable fractional volume of fluid per total tissue volume based on the attenuation and scattering coefficients determined for the second set of photons.

15. The method of claim 14, wherein the second wavelength is a non isobestic, second wavelength, of approximately 660 nm or approximately 970 nm where this second wavelength in combination with the first isobestic wavelength determine the $\alpha 800$ and $\alpha 660$ values combined with the S800 and S660 values where these values combined with their respective time derivatives determine the second constituent: a time-dependent, transmissive Oxygen Saturation measurement.

16. The method of claim 14, wherein a second wavelength is an isobestic, second wavelength, such as approximately 1300-1600 nm where this second wavelength in combination with the first isobestic wavelength determine the $\alpha 800$ and $\alpha 1300$ values and the S800 and S1300 values given by $$HCT = \frac{\left( \frac{dii8 - dS8'}{PL8} \right)}{xb13'} * \frac{2 * \alpha 8}{S8} - \Delta S8 \left( \frac{\alpha 8}{S8} \right)^2$$

where these values combined with their respective time derivatives determine a second constituent: a pulsatile, time-dependent, Hematocrit and Hemoglobin measurement.

17. The method of claim 14, wherein a second wavelength is an isobestic, second wavelength, of approximately 1300-1600 nm where this second wavelength in combination with the first isobestic wavelength determine the $\alpha 800$ and $\alpha 1300$ values and the S800 and S1300 values given by $$Xw = \frac{1 - \frac{HCT * (R138(1.04) + kw13)}{3 * kw13}}{\left( 1 - \frac{\Delta S13}{S13} \right)}$$

where these values combined with their respective time derivatives and Hematocrit determine a second constituent: a time-dependent, transmissive tissue water (Xw) measurement.

18. The method of claim 14, wherein a second wavelength is an isobestic, second wavelength, of approximately 1300-1600 nm used as $$d(i13) = (-1.5587 * (\max i13 * 1.2 * \alpha 8^{0.10}) + 27.55)^1$$

where the detected set of second photons determine the sensor alignment and tissue thickness, d, values.

19. An apparatus for non-invasively detecting at least a first constituent in blood while contained within animal body tissue, using data generated by a non-invasive photo-array including at least a first photo-emitter and at least first and second photo-detectors, wherein the first photo-emitter non-invasively propagates a first set of photons in the tissue at a single, isobestic, first wavelength, and the at least first and second photo-detectors detect the first set of photons following propagation into the fluid and emit signals in response thereto, and wherein the at least first photo-emitter and the at least first and second photo-detectors are in a known spatial arrangement, a computer program product comprising a computer usable storage medium having computer readable program code means embodied in the medium, the computer readable program code means comprising the steps of:
controlling the emission of at least a first set of photons in the tissue for transmission through or reflection by the blood and animal body tissue, wherein the first set of photons is controlled by the at least first photo-emitter at a single, isobestic, first wavelength;

a computer readable program code means for receiving the data stream from the at least first and second photo-detectors of the transmitted or reflected photons; and a computer readable program code means for determining the scattering coefficient (S) of the first set of photons in the fluid based on the first set of photons detected by the photo-detectors, and determining the attenuation coefficient ($\alpha$) of the first set of photons detected by the photo-detectors, for determining an amount of a first constituent in the fluid based on the attenuation and scattering coefficients determined for the first set of photons and determining fractional volume of fluid per total tissue volume (Xb) and determining tissue water fraction (Xw).

\* \* \* \* \*